United States Patent
Castillo et al.

(10) Patent No.: US 10,682,291 B2
(45) Date of Patent: *Jun. 16, 2020

(54) ENHANCED CO-FORMED MELTBLOWN FIBROUS WEB STRUCTURE AND METHOD FOR MANUFACTURING

(71) Applicant: The Procter & Gamble Company, Cincinnati, OH (US)

(72) Inventors: Mario Castillo, Cincinnati, OH (US); Steven Lee Barnholtz, West Chester, OH (US); Adam James Burt, Loveland, OH (US); Pamela Marie Morison, San Jose, CA (US)

(73) Assignee: The Procter & Gamble Company, Cincinnati, OH (US)

( * ) Notice: Subject to any disclaimer, the term of this patent is extended or adjusted under 35 U.S.C. 154(b) by 302 days.

This patent is subject to a terminal disclaimer.

(21) Appl. No.: 15/197,842

(22) Filed: Jun. 30, 2016

(65) Prior Publication Data

US 2017/0000695 A1 Jan. 5, 2017

Related U.S. Application Data

(60) Provisional application No. 62/186,750, filed on Jun. 30, 2015.

(51) Int. Cl.
*A61K 8/02* (2006.01)
*B32B 5/26* (2006.01)
(Continued)

(52) U.S. Cl.
CPC .............. *A61K 8/0208* (2013.01); *A47K 7/03* (2013.01); *A61K 8/731* (2013.01); *A61K 8/8111* (2013.01);
(Continued)

(58) Field of Classification Search
CPC .... A61K 8/0208; A61K 8/731; A61K 8/8111; B32B 2250/20; B32B 2250/40;
(Continued)

(56) References Cited

U.S. PATENT DOCUMENTS 4,100,324 A 7/1978 Anderson
4,355,066 A 10/1982 Newman
(Continued)

FOREIGN PATENT DOCUMENTS

EP  1 156 147 A1  11/2001
EP  2 456 585 B1  7/2013
JP  4641340 B2  3/2011

OTHER PUBLICATIONS

PCT International Search Report dated Sep. 28, 2016 (14 pages).
(Continued)

*Primary Examiner* — Jennifer A Steele
(74) *Attorney, Agent, or Firm* — Daniel S. Albrecht; Christian M. Best; William E. Gallagher

(57) ABSTRACT

An enhanced, co-formed fibrous web structure is disclosed. The web structure may have a co-formed core layer sandwiched between two scrim layers. The core layer may be formed of a blend of cellulose pulp fibers and melt spun filaments. The scrim layers may be formed of melt spun filaments. Filaments of one or both of the scrim layers, and optionally the core layer, may also be meltblown filaments. The core layer may include consolidated masses of cellulose pulp fibers to, for example, enhance texture and cleaning efficacy of a wet wipe made from the structure. The material forming the consolidated masses may be selected and/or processed so as to cause the masses to have reduced visual discernibility relative the surrounding areas of the structure, when the fibrous web structure is wetted. A method for
(Continued)

forming the structure, including formation and inclusion of the consolidated masses, is also disclosed.

21 Claims, 25 Drawing Sheets

(51) Int. Cl.

| | |
|---|---|
| D21H 27/00 | (2006.01) |
| B32B 5/02 | (2006.01) |
| D04H 1/56 | (2006.01) |
| D04H 3/14 | (2012.01) |
| D21H 13/14 | (2006.01) |
| A47K 7/03 | (2006.01) |
| B32B 5/08 | (2006.01) |
| B32B 29/00 | (2006.01) |
| B32B 7/05 | (2019.01) |
| D21H 27/30 | (2006.01) |
| A61K 8/73 | (2006.01) |
| A61K 8/81 | (2006.01) |
| A61Q 19/10 | (2006.01) |
| B32B 29/02 | (2006.01) |

(52) U.S. Cl.
CPC .............. *A61Q 19/10* (2013.01); *B32B 5/022* (2013.01); *B32B 5/08* (2013.01); *B32B 5/26* (2013.01); *B32B 7/05* (2019.01); *B32B 29/002* (2013.01); *B32B 29/02* (2013.01); *D04H 1/56* (2013.01); *D04H 3/14* (2013.01); *D21H 13/14* (2013.01); *D21H 27/005* (2013.01); *D21H 27/30* (2013.01); *A61K 2800/28* (2013.01); *B32B 2250/20* (2013.01); *B32B 2250/40* (2013.01); *B32B 2262/0253* (2013.01); *B32B 2262/06* (2013.01); *B32B 2262/062* (2013.01); *B32B 2262/067* (2013.01); *B32B 2262/14* (2013.01); *B32B 2307/54* (2013.01); *B32B 2307/718* (2013.01); *B32B 2307/726* (2013.01); *B32B 2307/728* (2013.01); *B32B 2432/00* (2013.01)

(58) Field of Classification Search
CPC ........ B32B 2260/021; B32B 2260/026; B32B 2260/04; B32B 2262/0253; B32B 2262/06; B32B 2262/062; B32B 2262/067; B32B 2262/14; B32B 2307/54; B32B 2307/718; B32B 2307/726; B32B 2307/728; B32B 2432/00; B32B 27/10; B32B 29/002; B32B 29/02; B32B 5/022; B32B 5/028; B32B 5/08; B32B 5/26; B32B 7/045; B32B 7/14; D04H 13/00; D04H 1/56; D04H 3/14; D04H 3/163; Y10T 442/00

See application file for complete search history.

(56) References Cited

U.S. PATENT DOCUMENTS

| | | | |
|---|---|---|---|
| 4,370,289 A | 1/1983 | Sorenson | |
| 4,436,780 A | 3/1984 | Hotchkiss | |
| 4,604,313 A | 8/1986 | McFarland et al. | |
| 4,623,576 A | 11/1986 | Lloyd | |
| 4,675,226 A | 6/1987 | Ott | |
| 4,774,125 A | 9/1988 | McAmish | |
| 4,784,892 A | 11/1988 | Storey | |
| 4,885,202 A | 12/1989 | Lloyd | |
| 4,906,513 A | 3/1990 | Kebbell | |
| 4,931,201 A | 6/1990 | Julemont | |
| 5,204,165 A | 4/1993 | Schortmann | |
| 5,316,601 A | 5/1994 | Hebbard | |
| 5,350,624 A * | 9/1994 | Georger | D04H 1/56 139/420 B |
| 5,455,110 A * | 10/1995 | Connor | B32B 5/26 442/382 |
| 5,683,794 A | 11/1997 | Wadsworth | |
| 5,834,385 A | 11/1998 | Blaney | |
| 5,914,084 A | 6/1999 | Benson et al. | |
| 5,948,710 A | 9/1999 | Pomplum | |
| 5,962,112 A | 10/1999 | Haynes | |
| 6,013,223 A | 1/2000 | Schwarz | |
| 6,028,018 A | 2/2000 | Amundson | |
| 6,177,370 B1 | 6/2001 | Skoog | |
| 6,361,784 B1 | 3/2002 | Brennan et al. | |
| 6,488,801 B1 | 12/2002 | Bodaghi | |
| 6,494,974 B2 | 12/2002 | Riddell | |
| 6,589,892 B1 | 7/2003 | Smith | |
| 6,861,380 B2 | 3/2005 | Garnier | |
| 6,926,931 B2 | 8/2005 | Qashou | |
| 7,278,187 B2 | 10/2007 | Petersen | |
| 7,381,299 B2 | 6/2008 | Shannon | |
| 7,425,517 B2 | 9/2008 | Deka | |
| 7,645,353 B2 | 1/2010 | Thomaschefsky | |
| 7,879,191 B2 | 2/2011 | Dyer | |
| 9,408,761 B2 | 8/2016 | Xu et al. | |
| 9,944,047 B2 * | 4/2018 | Burt | B32B 5/26 |
| 2003/0010091 A1 | 1/2003 | Tungare | |
| 2003/0211802 A1 | 11/2003 | Keck | |
| 2003/0224686 A1 | 12/2003 | Anderson | |
| 2005/0130536 A1 | 6/2005 | Siebers | |
| 2005/0136772 A1 | 6/2005 | Chen | |
| 2005/0148261 A1* | 7/2005 | Close | A61K 8/0208 442/381 |
| 2005/0148262 A1 | 7/2005 | Verona | |
| 2005/0245159 A1 | 11/2005 | Chmeilewski | |
| 2008/0248239 A1 | 10/2008 | Pomeroy | |
| 2009/0023839 A1 | 1/2009 | Barnholtz et al. | |
| 2009/0084513 A1 | 4/2009 | Barnholtz et al. | |
| 2009/0151748 A1 | 6/2009 | Ridenhour | |
| 2010/0048082 A1 | 2/2010 | Topolkaroev | |
| 2010/0163200 A1 | 7/2010 | Dougherty et al. | |
| 2011/0045261 A1 | 2/2011 | Sellars | |
| 2011/0104970 A1* | 5/2011 | Barnholtz | D04H 1/407 442/1 |
| 2011/0244199 A1 | 10/2011 | Brennan | |
| 2012/0177888 A1* | 7/2012 | Escafere | B32B 5/26 428/162 |
| 2014/0039434 A1 | 2/2014 | Xu et al. | |
| 2015/0086760 A1 | 3/2015 | Castillo | |
| 2015/0322601 A1 | 11/2015 | Satpal | |
| 2017/0002486 A1 | 1/2017 | Castillo et al. | |
| 2017/0022643 A1 | 1/2017 | Burt et al. | |
| 2018/0002848 A1* | 1/2018 | Burt | B32B 5/022 |

OTHER PUBLICATIONS

All Office Actions, U.S. Appl. No. 15/197,878.
All Office Actions, U.S. Appl. No. 15/197,895.
All Office Actions, U.S. Appl. No. 15/197,947.
U.S. Appl. No. 15/197,878, filed Jun. 30, 2016, Castillo et al.
U.S. Appl. No. 15/197,895, filed Jun. 30, 2016, Burt et al.
U.S. Appl. No. 15/197,947, filed Jun. 30, 2016, Burt et al.

* cited by examiner

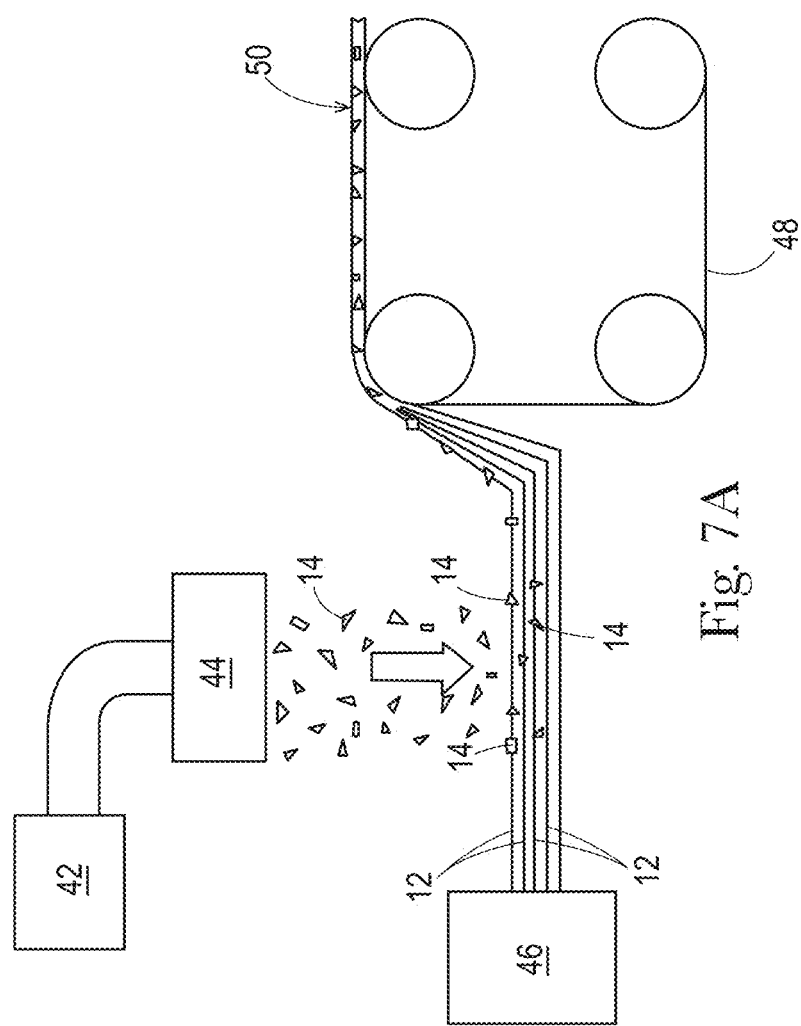

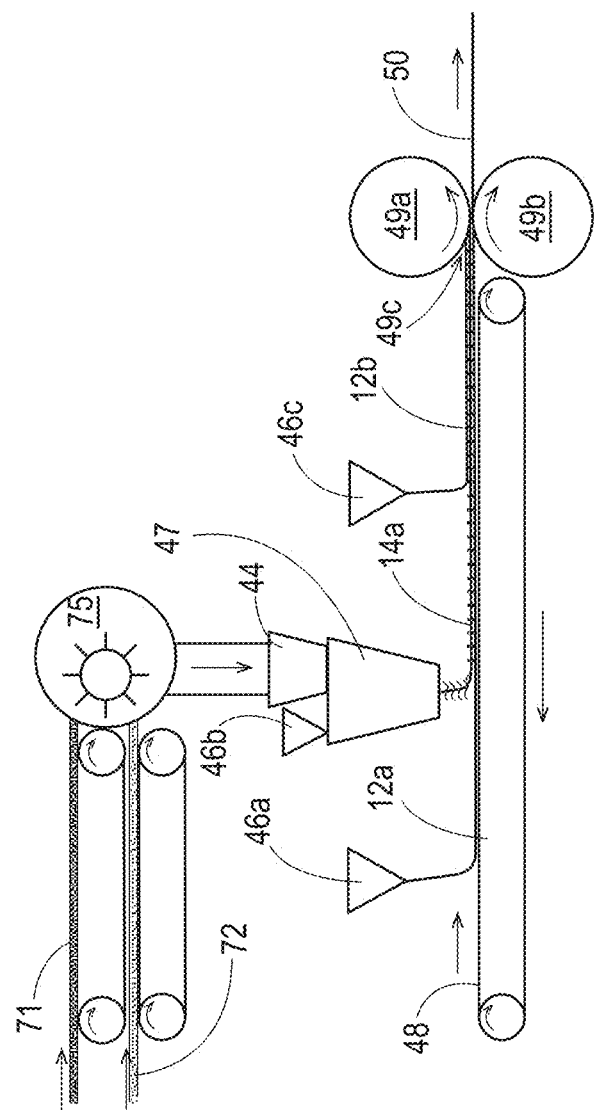

Wet Cross Direction Peak Tensile Strength (Newtons)
Shaded Bands: Predictive Model
144 Topmost band = >10
143 Second band = 8-10
142 Third band = 6-8
141 Bottom band = 4-6

Wet Machine Direction Peak Tensile Strength (Newtons)

Shaded Bands: Predictive Model
    148 Topmost band =  >16.5
    147 Second band =  14 - 16.5
    146 Third band =     11.5 - 14.5
    145 Bottom band =  9 - 11.5

Consumer Preference Indication (Panel Rating)

Shaded Bands: Predictive Model (60 gsm)
    174 Middle band =                 >2.3
    173 Second from middle band =   2 - 2.3
    172 Third from middle band =     1.5 - 2
    171 Fourth from middle band =   0.7 - 1.5
    170 Outer band =                (-1) - 0.7

ENHANCED CO-FORMED MELTBLOWN FIBROUS WEB STRUCTURE AND METHOD FOR MANUFACTURING

CROSS REFERENCE TO RELATED APPLICATION

This application claims the benefit of U.S. Provisional application No. 62/186,750, filed Jun. 30, 2015, the substance of which is incorporated herein by reference.

BACKGROUND OF THE INVENTION

Disposable wet wipes products are manufactured and sold for personal cleansing needs in circumstances where a source of water, soap and cleaning cloth may be desired but are unavailable or inconvenient. An example of a wet wipes product is PAMPERS brand baby wipes, manufactured and sold by The Procter & Gamble Company for use in cleaning a baby's skin during a diaper change. The product includes a stacked supply of wipes formed of a suitable fibrous web structure pre-cut into individual sheets, and moistened with a suitable lotion formula. The lotion formula may be aqueous and may contain a variety of ingredients selected to aid in skin cleansing and to provide other benefits. The moistened supply of wipes is typically packaged in a rigid dispensing tub or dispensing package of flexible film, designed to effectively retain the moisture in the lotion after package opening, for the period of time expected for use of the entire supply. Wet wipes products are also manufactured and sold for other skin cleansing needs.

To be suitable for making a wet wipes product, the fibrous web structure should be capable of retaining a certain amount of structural integrity when wetted, i.e., it should not disintegrate like a typical cellulose pulp fiber-based material when wetted (like, e.g., typical rolled bathroom tissue products), and it should have a relatively soft feel. For these reasons, substrates used to make wet wipes products have often been formed largely of synthetic polymer components and structures that do not dissolve or disintegrate in water. Although such substrates desirably retain structural integrity and feel soft when wetted, they tend to be less absorbent and have relatively low-friction surface properties that render them less desirable as cleaning media (e.g., they may be more slippery and less likely to pick up soil), than cellulose fiber-based substrates.

Recently, hybrid "coform" substrates formed of blends of cellulose pulp fibers and synthetic polymer fibers have been used to make wet wipes products. Due to their naturally greater hydrophilicity, and to the greater coefficient of friction and surface texture they impart, the pulp fibers impart desirable absorbency properties and surface cleaning abilities to the fibrous web structure. The polymer fibers (together with other features added in processing) can help impart wet structural integrity.

More recently, improvements have been introduced to the co-forming process and resulting fibrous web structure. As described in U.S. application Ser. No. 13/076,492, a co-formed fibrous web structure with improved absorption properties is described. In addition to the other improvements described in that application, it is briefly surmised that layers formed of meltblown polymer filaments alone can be formed on the outermost surfaces of the co-formed batt prior to bonding, to beneficial effect. It is surmised that the addition of the meltblown layer (called "scrim") can help reduce release of lint (comprising fibers dislodged from the structure) during use by a consumer.

However, the ways in which inclusion of scrim layers, and the relative proportions of components of the scrim layers and intermediate or core layers, affect properties such as tensile strength, drape, surface friction, opacity, texture and feel of the web material, have not been apparent or predictable. Thus, it would be beneficial if the best proportions of components overall, together with their allocations among the various layers or substructures, of a fibrous web structure having scrim layers, for use as wet wipe, could be identified. Further, although adding scrim layers to a co-formed structure can enhance some properties of the structure, to some consumers the scrim layers may reduce a desired perception of surface friction or roughness they may associate with cleaning efficacy, attributable to the presence of exposed pulp fibers at the surface.

Thus, there remains room for improvements in wet wipes substrates that incorporate the advantages of the hybrid pulp and polymer combination, while improving mechanical strength, reducing incidence of shedding/dislodgement of pulp fibers, and providing other improvements that may be beneficial.

BRIEF DESCRIPTION OF THE DRAWINGS

FIG. 7A is a schematic illustration of an example of a system and process for making a fibrous web structure.

FIG. 7B is a schematic illustration of another example of a system and process for making a fibrous web structure.

DETAILED DESCRIPTION OF EMBODIMENTS

Definitions

Figure 1:
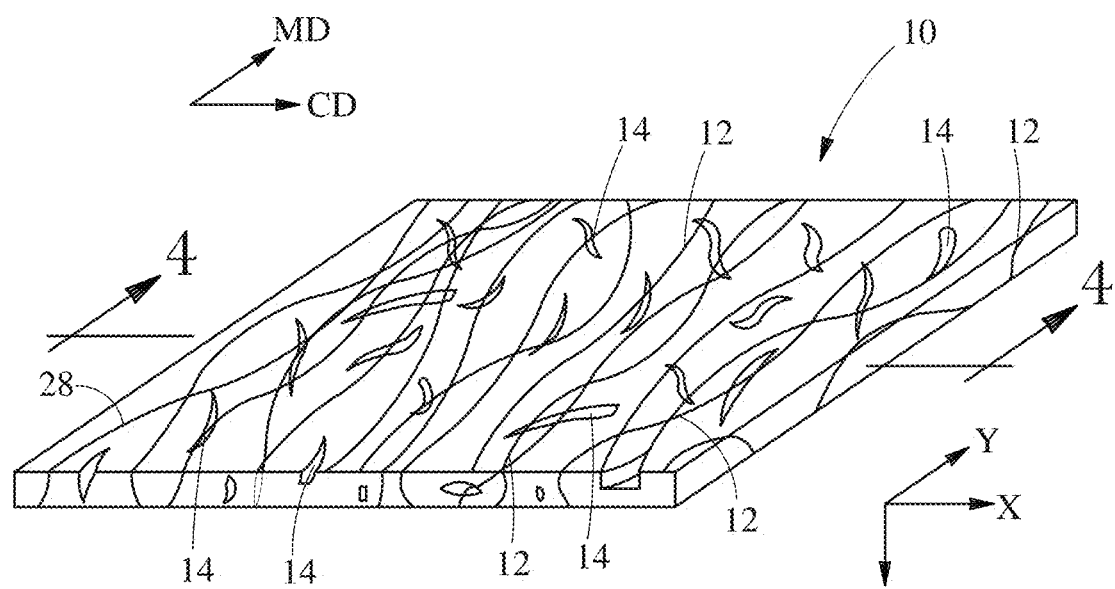
FIG. 1 is a schematic perspective illustration of an example of a fibrous web structure.

As used herein, the articles "a" and "an" when used herein, for example, "an anionic surfactant" or "a fiber" is understood to mean one or more of the material that is claimed or described.

"Basis Weight" is the weight per unit surface area (in a machine-direction/cross-direction plane) of a sample of web material (on one side), expressed in grams/meter$^2$ (gsm). Basis weight may be specified in manufacturing specifications, and also may be measured, and reflects the weight of the material prior to addition of any liquid composition.

"Co-formed fibrous web structure" as used herein means that the fibrous web structure comprises an intermixed and/or entangled blend of at least two different materials wherein at least one of the materials comprises filaments, such as spun polymer filament (e.g., filaments spun from polypropylene resin), and at least one other material, different from the first material, comprises fibers. In one example, a co-formed fibrous web structure comprises fibers, such as cellulose or wood pulp fibers, and filaments, such as spun polypropylene filaments. A co-formed fibrous web structure may also comprise solid particulate additives such as but not limited to absorbent gel materials, filler particles, particulate spot bonding powders or clays.

"Cross Direction" or "CD" with respect to a fibrous web structure means the direction perpendicular to the predominant direction of movement of the fibrous web structure through its manufacturing line.

"Fiber" means an elongate particulate having a limited length exceeding its width or diameter, i.e. a length to width ratio of no more than 200. For purposes of the present disclosure, a "fiber" is an elongate particulate as described above that has a length of less than 3 cm. Fibers are typically considered discontinuous in nature. Non-limiting examples of fibers include hardwood and softwood pulp fibers; hemp bast; bagasse; bamboo; corn stalk; cotton; cotton stalk; cotton linters; esparto grass; flax tow; jute bast; kenaf bast; reed; rice straw; sisal; switch grass; wheat straw; and synthetic staple (i.e., cut or chopped) spun fibers made from polyester, nylons, rayon (including viscose and lyocell); polyolefins such as polypropylene and polyethylene, natural polymers, such as starch, starch derivatives, cellulose and cellulose derivatives, hemicellulose, hemicellulose derivatives, chitin, chitosan, polyisoprene (cis and trans), peptides, polyhydroxyalkanoates, copolymers of polyolefins such as polyethylene-octene, and biodegradable or compostable thermoplastics such as polylactic acid, polyvinyl alcohol, and polycaprolactone. Synthetic fibers may be monocomponent or multicomponent, e.g., bicomponent. For purposes herein, "long fibers" have an average length exceeding 10 mm; "medium length fibers" have an average length of from 2 mm and 10 mm; and "short fibers" have an average length less than 2 mm.

"Fibrous web structure" as used herein means a web or sheet structure formed of one or more types of filaments and/or fibers. The term "fibrous web structure" encompasses nonwovens.

A "filament" is an elongate particulate having a theoretically unlimited length, but at least a length-to-width and/or length-to-diameter ratio greater than 500 and a length greater than 5.08 cm. Filaments are typically spun in a continuous process, and are, therefore, considered substantially "continuous" in nature, having an indeterminate length. Non-limiting examples of filaments include meltspun/meltblown or spunbond filaments spun from polymer resin. Non-limiting examples of materials that can be spun into filaments include natural polymers, such as starch, starch derivatives, cellulose and cellulose derivatives, hemicellulose, hemicellulose derivatives, chitin, chitosan, polyisoprene (cis and trans), peptides, polyhydroxyalkanoates, and synthetic polymers including, but not limited to, thermoplastic polymers, such as polyesters, nylons, polyolefins such as polypropylene, polyethylene, polyvinyl alcohol and polyvinyl alcohol derivatives, sodium polyacrylate (absorbent gel material), and copolymers of polyolefins such as polyethylene-octene, and biodegradable or compostable thermoplastic fibers such as polylactic acid, polyvinyl alcohol, and polycaprolactone. Filaments may be monocomponent or multicomponent, e.g., bicomponent.

"Like chemistry," with respect to two polymers, two blends of polymers, or a polymer and a blend of polymers, means that the two polymers, two blends of polymers, or a polymer and a blend of polymers, are capable of mixing at a temperature of 250° C. or lower, to form a single thermodynamic phase.

"Liquid composition" refers to any liquid, including, but not limited to a pure liquid such as water, an aqueous solution, a colloid, an emulsion (including oil-in-water and water-in-oil), a suspension, a solution and mixtures thereof. The term "aqueous solution" as used herein, refers to a solution that is at least about 20%, at least about 40%, or even at least about 50% water by weight, and is no more than about 95%, or no more than about 90% water by weight. The term "liquid composition" encompasses a lotion or other cleaning or skin conditioning formulation that may be included with wet wipes.

"Machine Direction" or "MD" with respect to a fibrous web structure means the direction parallel to the predominant direction of movement of the fibrous web structure through its manufacturing line.

"Meltblown" and forms thereof refer to a process of making filaments and webs thereof, in which filaments are spun by extruding streams of molten polymer resin under pressure through one or more spinnerets, and then substantially attenuating (elongating and reducing diameter and/or width of) the polymer streams following their exit from the spinnerets, with one or more high-velocity streams of heated air proximate the exits of the spinnerets. The air handling equipment (such as a manifold) may be a separate or integral part of the spinneret and is configured to direct the air stream(s) along path(s) at least partially parallel to the direction of extrusion of the polymer streams. Meltblown filaments are distinguished from polymer filaments made by other spunbond or melt-spinning processes by their comparatively very small diameter and/or very small width, imparted by the attenuating air streams, and typically have an average diameter or width of from 0.1 µm to 30 µm, 15 µm, 10 µm or even 5 µm. Following attenuation, the filaments may be air quenched with cooling air, or mist quenched with a mixture of cooling air and water droplets. The spun, attenuated and quenched fibers are then typically directed toward and accumulated in somewhat random, varying and entangled orientation on, a moving belt or rotating drum, to form a web.

"Nonwoven" for purposes herein means a consolidated web of fibers, continuous filaments, or chopped or staple fibers of any nature or origin, or any blend thereof, which have been formed into a web, and bonded together by any means, with the exception of weaving or knitting. A nonwoven is an example of a fibrous web structure. "Nonwoven" does not include nonfibrous skin-like or membrane-like materials with a continuous structure sometimes identified or described as "films". "Nonwoven" does not include a product, such as paper, in which cellulose pulp fibers are distributed via a wetlaying process to form a sheet or web, without the need for any post-formation bonding processes to complete formation of the sheet or web.

"Particulate" as used herein means a granular substance or powder.

"Predominate" or a form thereof, with respect to a proportion of a component of a structure or composition, means that the component constitutes the majority of the weight of the structure or composition.

"Pre-moistened" and "wet" are used interchangeably herein and refer to fibrous web structures and/or wipes which are moistened with a liquid composition prior to packaging, and may be packaged in an effectively moisture impervious container or wrapper. Such pre-moistened wipes, which can also be referred to as "wet wipes," may be suitable for use for cleaning a baby's skin (such, as, e.g., during a diaper change), as well the skin of older children and adults.

"Stack" refers to an orderly pile of individually cut portions of fibrous web structure, e.g., wipes. Based upon the assumption that there are at least three wipes in a stack, each wipe, except for the topmost and bottommost wipes in the stack, will be in direct contact with the wipe directly above and below itself in the stack. Moreover, when viewed from above, the wipes will be layered on top of each other, or superimposed, such that only the topmost wipe of the stack will be visible. The height of the stack is measured from the bottom of the bottommost wipe in the stack to the top of the topmost wipe in the stack and is provided in units of millimeters (mm).

"Surfactant" as used herein, refers to materials which preferably orient toward an interface. Surfactants include the various surfactants known in the art, including: nonionic surfactants; anionic surfactants; cationic surfactants; amphoteric surfactants, zwitterionic surfactants; and mixtures thereof.

"Visually discernible," with respect to consolidated masses of fibers included in a fibrous web structure, means that the masses may be visually identified and located on the structure by an adult human being with normal vision and color perception, observing the structure at a 45-degree angle from a distance of 2 feet, as it is laying on a horizontal black surface under inside standard modern daytime office lighting conditions.

Herein, where the quantity of a component of a fibrous web structure is expressed in "X weight percent" or "X percent by weight," or an abbreviated or shortened form thereof, the quantity means that the component's weight constitutes X percent of the total weight of the fibrous web structure.

"z-direction" with respect to a web or a fibrous web structure means the direction orthogonal to the plane defined by the machine direction and cross direction of the web or fibrous web structure.

Unless otherwise noted, all component or composition levels are in reference to the active level of that component or composition, and are exclusive of impurities, for example, residual solvents or by-products, which may be present in commercially available sources.

Fibrous Web Structure

A fibrous web structure within the scope of the present invention may have a basis weight between about 10 gsm to about 120 gsm and/or from about 20 gsm to about 110 gsm and/or from about 30 gsm to about 100 gsm and/or from about 40 to 90 gsm. For purposes of use for making baby wipes, from product testing and consumer research it is believed that a fibrous web structure as disclosed herein having a basis weight from 40 gsm to 90 gsm and more preferably from 45 gsm to 85 gsm strikes the best balance between thickness/caliper, absorption capacity, opacity, drape and feel, and tensile strength, on one hand, and economy, on the other hand.

The fibrous web structure may include additives such as softening agents, temporary wet strength agents, permanent wet strength agents, bulk softening agents, silicones, wetting agents, latexes, especially surface-pattern-applied latexes, dry strength agents such as carboxymethylcellulose and starch, and other types of additives suitable for inclusion in and/or on fibrous web structures.

Fibrous web structures with the scope of the present invention may be formed of a plurality of filaments, a plurality of fibers, and a mixture of filaments and fibers.

Figure 2:
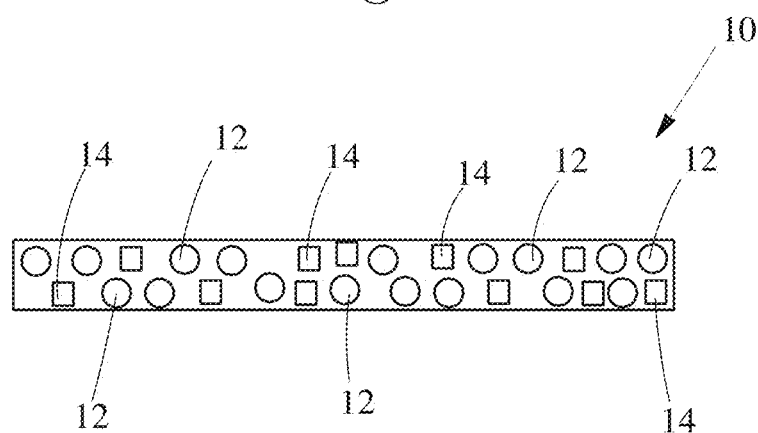
FIG. 2 is a schematic, cross-sectional representation of FIG. 1 taken along line 4-4.

FIGS. 1 and 2 show schematic representations of an example of a fibrous web structure.

Fibers useful as components of the fibrous web structure include cellulosic fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred since they impart a superior tactile sense of softness to tissue sheets made therefrom. Pulps derived from both angiosperm (flowering) trees (hereinafter, also referred to as "hardwood") and gymnosperm (coniferous) trees (hereinafter, also referred to as "softwood") may be utilized. The hardwood and softwood fibers can be blended, or alternatively, can be deposited in layers to provide a stratified web. U.S. Pat. Nos. 4,300,981 and 3,994,771 are incorporated herein by reference for the purpose of disclosing layering of hardwood and softwood fibers. Also applicable are fibers derived from recycled paper, which may contain any or all of the above categories as well as other non-fibrous materials such as fillers and adhesives used to facilitate the original papermaking.

A blend of long, or medium-length, pulp fibers, and short pulp fibers may be suitable for purposes herein. Generally, long and medium-length fibers tend to be larger and more coarse, providing desirable texture and absorption characteristics, while short fibers tend to be finer and softer, enhancing opacity of the structure and adding tactile softness. Including short pulp fibers as a portion of the fiber blend may be beneficial for controllably including consolidated masses of fibers in the blend.

In one example, a blend of softwood pulp fibers (medium-length) and hardwood pulp fibers (short) may be used. The softwood and hardwood pulp fibers, or medium-length and short fibers, may be included in a weight ratio of 20:80 to 90:10. For purposes herein, it may be desired that the weight ratio of softwood fibers to hardwood fibers, or weight ratio of medium-length fibers to short fibers, be from 60:40 to 90:10, more preferably 65:35 to 85:15, and still more preferably 70:30 to 80:20 in the structure. In a more particular example within these ranges, the softwood pulp fibers may be SSK (southern softwood kraft) pulp fibers. In another more particular example within these ranges, the hardwood pulp fibers may be birch, aspen or *Eucalyptus* pulp fibers. In a still more particular example within these ranges, the softwood pulp fibers may be SSK pulp fibers and the hardwood pulp fibers may be birch, aspen or *Eucalyptus* pulp fibers. Aspen, birch or *Eucalyptus* pulp fibers may be desirable for their fineness, shortness, and softness, which contribute to enhancing opacity and softness of the fibrous web structure, and *Eucalyptus* pulp may be particularly preferred for these characteristics.

In addition to the various wood pulp fibers, other cellulosic fibers such as cotton linters, rayon, lyocell, viscose and bagasse may be used. Other sources of cellulose in the form of fibers or materials capable of being spun into fibers include grasses and grain sources.

As shown in FIGS. 1 and 2, the fibrous web structure 10 may be a co-formed fibrous web structure. The fibrous web structure 10 comprises a plurality of filaments 12, such as polypropylene filaments, and a plurality of fibers, such as wood pulp fibers 14. The filaments 12 may be randomly arranged as a result of the process by which they are spun and/or formed into the fibrous web structure 10. The wood pulp fibers 14, may be randomly dispersed throughout the fibrous web structure 10 in the x-y (machine-direction/cross-direction) plane. The wood pulp fibers 14 may be non-randomly dispersed throughout the fibrous web structure in the z-direction. In one example (not shown), the wood pulp fibers 14 are present at a higher concentration on one or more of the exterior, x-y plane surfaces than within the fibrous web structure along the z-direction.

Figure 3:
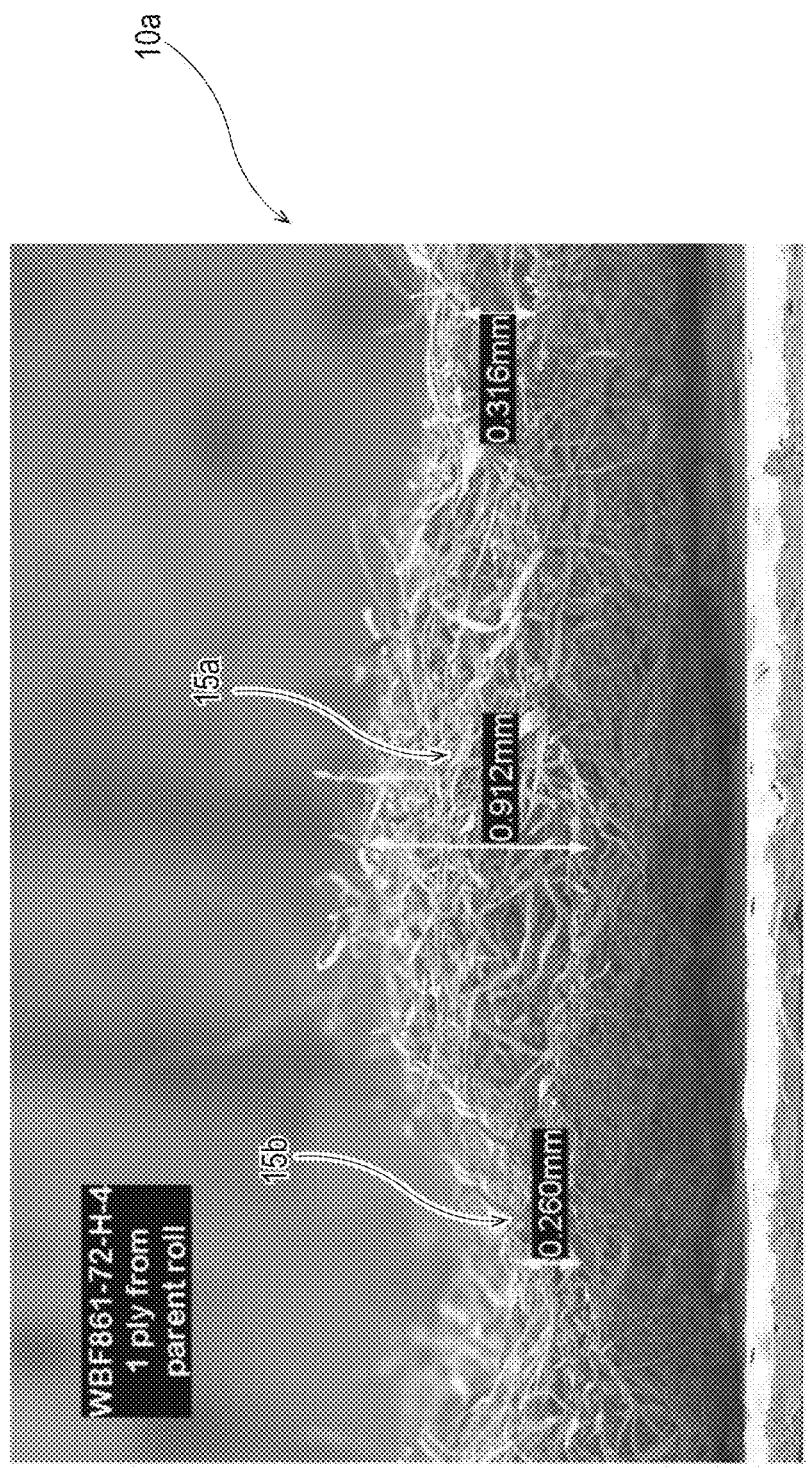
FIG. 3 is a scanning electron microscope image of a cross-section of an example of fibrous web structure.

FIG. 3 shows a cross-sectional, scanning electron microscope image of an example of a fibrous web structure 10a including a non-random, repeating pattern of microregions 15a and 15b. The microregion 15a (typically referred to as a "pillow") exhibits a different value of a localized property than microregion 15b (typically referred to as a "knuckle"). In one example, the microregion 15b is a continuous or semi-continuous network and the microregion 15a are discrete regions within the continuous or semi-continuous network. The localized property may be caliper. In another example, the localized property may be density.

Figure 4:
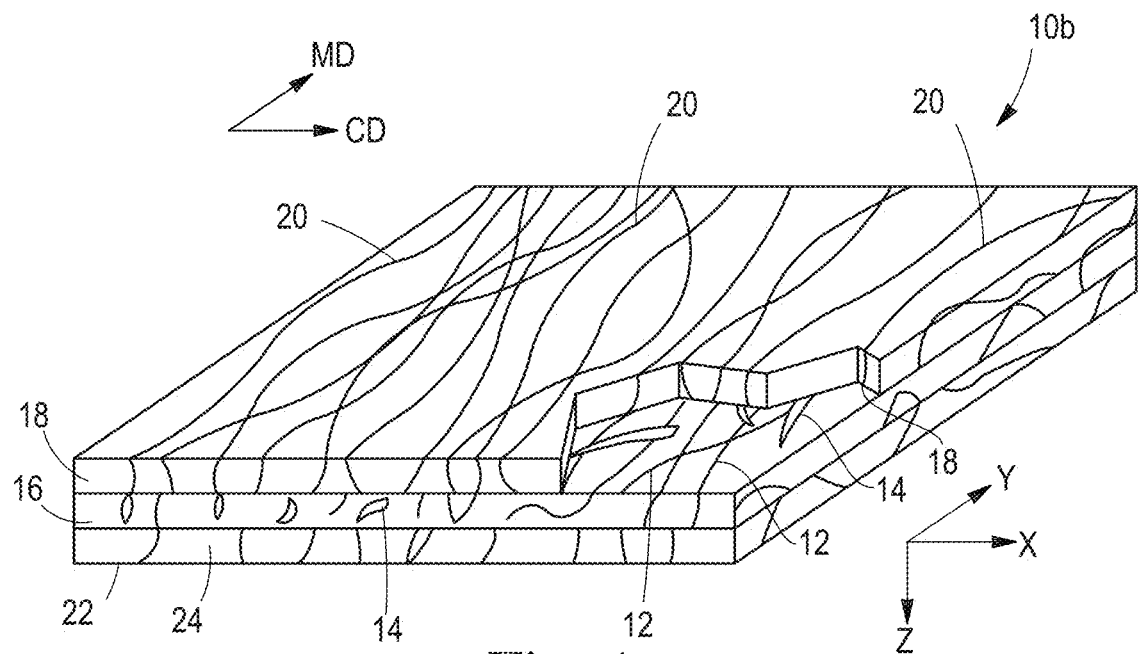
FIG. 4 is a schematic, perspective illustration of an example of a fibrous web structure.

As shown in FIG. 4, another example of a fibrous web structure is a layered fibrous web structure 10b. The layered fibrous web structure 10b includes a first layer 16 comprising a plurality of filaments 12, such as polypropylene filaments, and a plurality of fibers, in this example, wood pulp fibers 14. The layered fibrous web structure 10b further comprises a second layer 18 comprising a plurality of filaments 20, such as polypropylene filaments. In one example, the first and second layers 16, 18, respectively, are sharply defined zones of concentration of the filaments and/or fibers. The plurality of filaments 20 may be deposited directly onto a surface of the first layer 16 to form a layered fibrous web structure that comprises the first and second layers 16, 18, respectively.

Further, the layered fibrous web structure 10b may comprise a third layer 22, as shown in FIG. 4. The third layer 22 may comprise a plurality of filaments 24, which may be the same or different from the filaments 20 and/or 16 in the second 18 and/or first 16 layers. As a result of the addition of the third layer 22, the first layer 16 is positioned, for example sandwiched, between the second layer 18 and the third layer 22. The plurality of filaments 24 may be deposited directly onto a surface of the first layer 16, opposite from the second layer, to form the layered fibrous web structure 10b that comprises the first, second and third layers 16, 18, 22, respectively.

Figure 5:
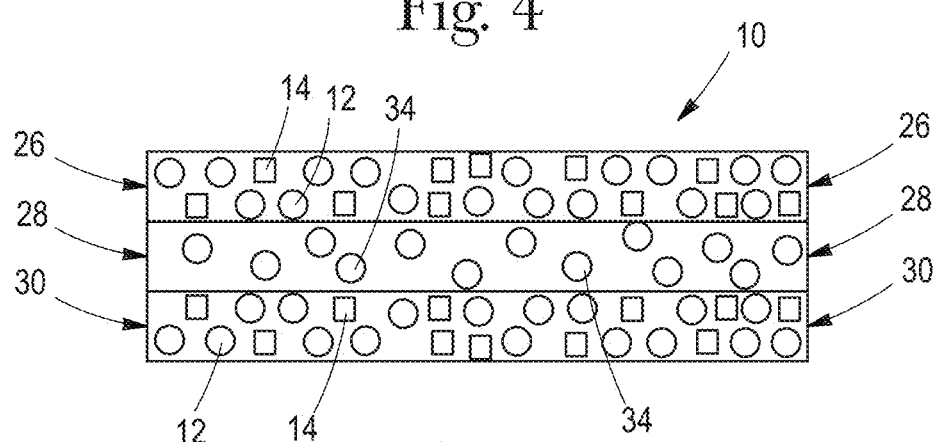
FIG. 5 is a schematic, cross-sectional representation of an example of a fibrous web structure.

FIG. 5 is a cross-sectional schematic illustration of another example of a fibrous web structure comprising a layered fibrous web structure 10c. The layered fibrous web structure 10c includes a first layer 26, a second layer 28 and optionally a third layer 30. The first layer 26 may comprise a plurality of filaments 12, such as polypropylene filaments, and a plurality of fibers, such as wood pulp fibers 14. The second layer 28 may comprise any suitable filaments, fibers and/or polymeric films. In one example, the second layer 28 comprises a plurality of filaments 34. In one example, the filaments 34 comprise a polymer selected from the group consisting of: polysaccharides, polysaccharide derivatives, polyvinylalcohol, polyvinylalcohol derivatives and mixtures thereof.

In yet another example, a fibrous web structure may include two outer layers consisting of 100% by weight filaments and an inner layer consisting of 100% by weight fibers.

In another example, instead of being layers of fibrous web structure 10c, the material forming layers 26, 28 and 30, may be in the form of layers wherein two or more of the layers may be combined to form a fibrous web structure. The layers may be bonded together, such as by thermal bonding and/or adhesive bonding, to form a multi-layer fibrous web structure.

Figure 6A:
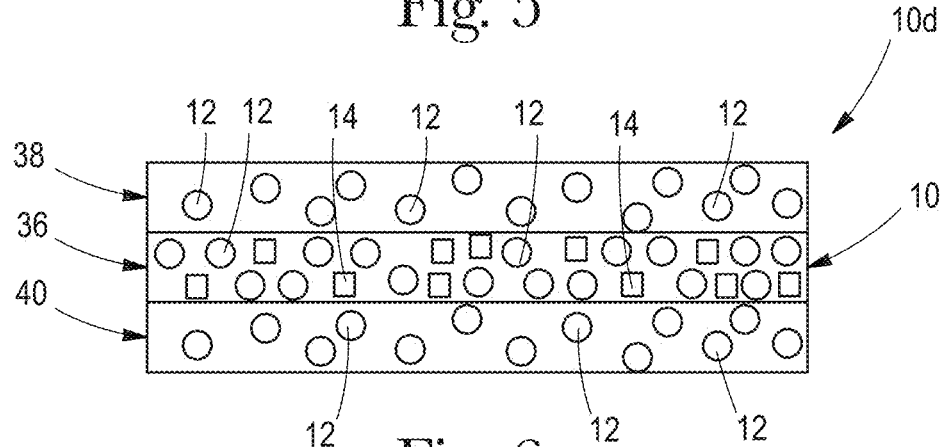
FIG. 6A is a schematic, cross-sectional illustration of an example of a fibrous web structure.

Another example of a fibrous web structure is schematically illustrated in FIG. 6A. The fibrous web structure 10d may comprise two or more layers, wherein one layer 36 comprises any suitable fibrous web structure in accordance with the present disclosure, for example fibrous web structure 10 as shown in FIGS. 1 and 2 and another layer 38 comprising any suitable fibrous web structure, for example a fibrous web structure comprising filaments 12, such as polypropylene filaments. The fibrous web structure of layer 38 may be in the form of a net, mesh, scrim or other structure that includes pores that expose one or more portions of the fibrous web structure 10d to an external environment and/or at least to liquids that may come into contact, at least initially, with the fibrous web structure of layer 38. In one example, layer 38 may be a layer of scrim formed of a deposit of somewhat, or substantially, randomly laid and/or accumulated meltblown polymer filaments.

In addition to layer 38, the fibrous web structure 10d may further comprise layer 40. Layer 40 may comprise a fibrous web structure comprising filaments 12, such as polypropylene filaments, and may be the same or different from the fibrous web structure of layer 38.

Two or more of the layers 36, 38 and 40 may be bonded together, such as by thermal bonding and/or adhesive bonding, to form a multi-layer fibrous web structure. After a bonding operation, especially a thermal bonding operation, it may be difficult to distinguish the layers of the fibrous web structure 10d and the fibrous web structure 10d may visually and/or physically be similar to a layered fibrous web structure in that one would have difficulty separating the once individual layers from each other. In one example, layer 36 may comprise a fibrous web structure that exhibits a basis weight of at least about 15 gsm and/or at least about 20 gsm and/or at least about 25 gsm and/or at least about 30 gsm up to about 120 gsm and/or 100 gsm and/or 80 gsm and/or 60 gsm and the layers 38 and 42, when present, independently and individually, may comprise fibrous web structures that exhibit basis weights of less than about 10 gsm and/or less than about 7 gsm and/or less than about 5 gsm and/or less than about 3 gsm and/or less than about 2.5 gsm, or from greater than 0 gsm to less than about 2.5 gsm, or from 0.5 gsm to 2.5 gsm.

Layers 38 and 40, when present, may help retain the fibers, in this case the wood pulp fibers 14, on and/or within the fibrous web structure of layer 36 thus reducing lint and/or dust (as compared to a single-layer fibrous web structure comprising the fibrous web structure of layer 36 without the layers 38 and 40) resulting from the wood pulp fibers 14 becoming free from the fibrous web structure of layer 36.

Figure 6B:
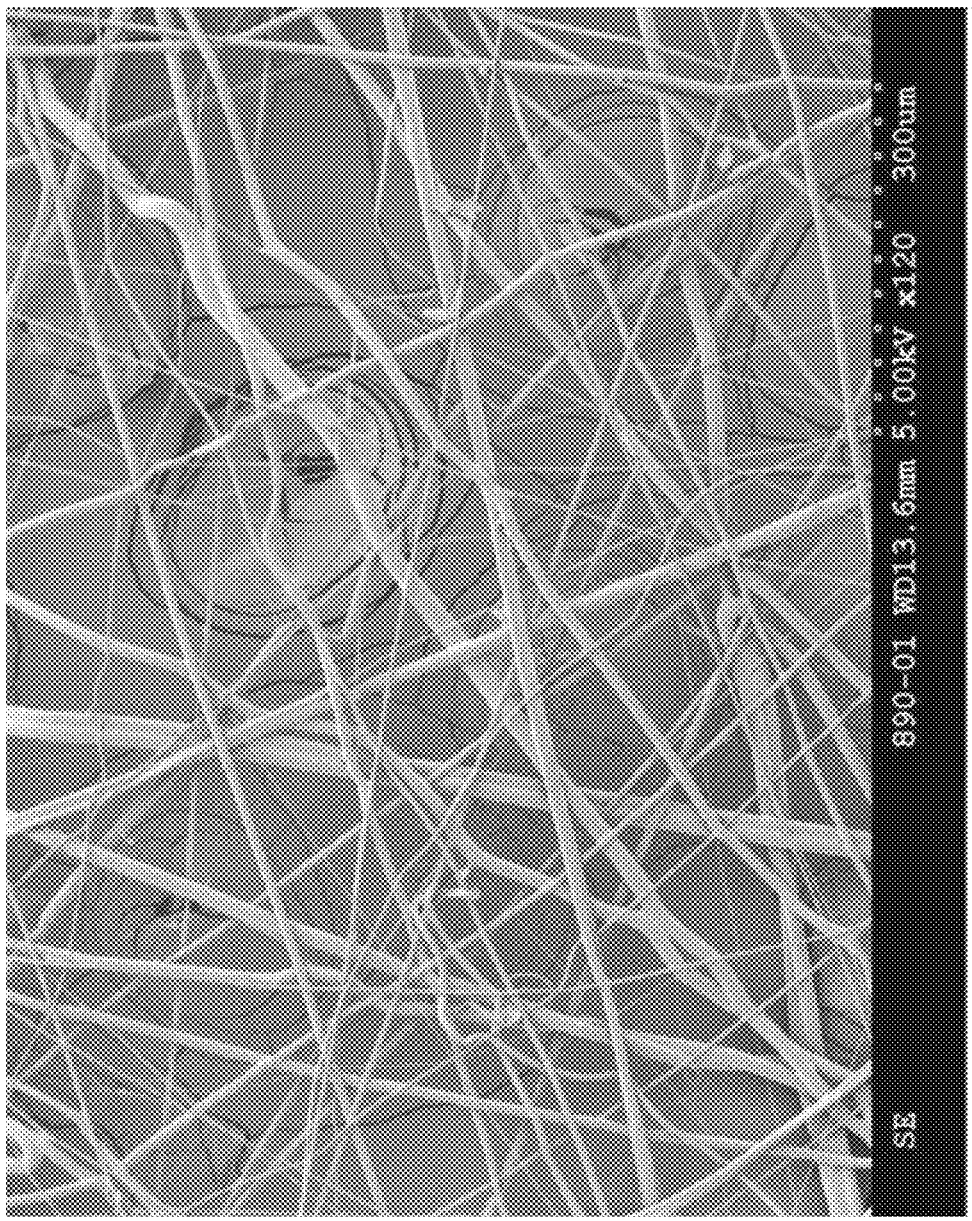
FIG. 6B is a scanning electron microscope image of a plan view of an example of scrim formed of meltblown filaments (overlying an unrelated supporting surface).

FIG. 6B is a scanning electron microscope image of a plan view of an example of scrim layer (overlying an unrelated supporting surface) that may be formed in a meltblowing process, creating a network of substantially randomly-laid, continuous fine filaments. The thickness and basis weight of the layer may be controlled by controlling the rate of throughput of polymer resin through the meltblowing equipment, and the rate of speed of the collecting belt, drum or other surface upon which the filaments are collected after spinning. In FIG. 6B it can be seen that the filaments create a highly porous network of fine filaments.

Figure 6C:
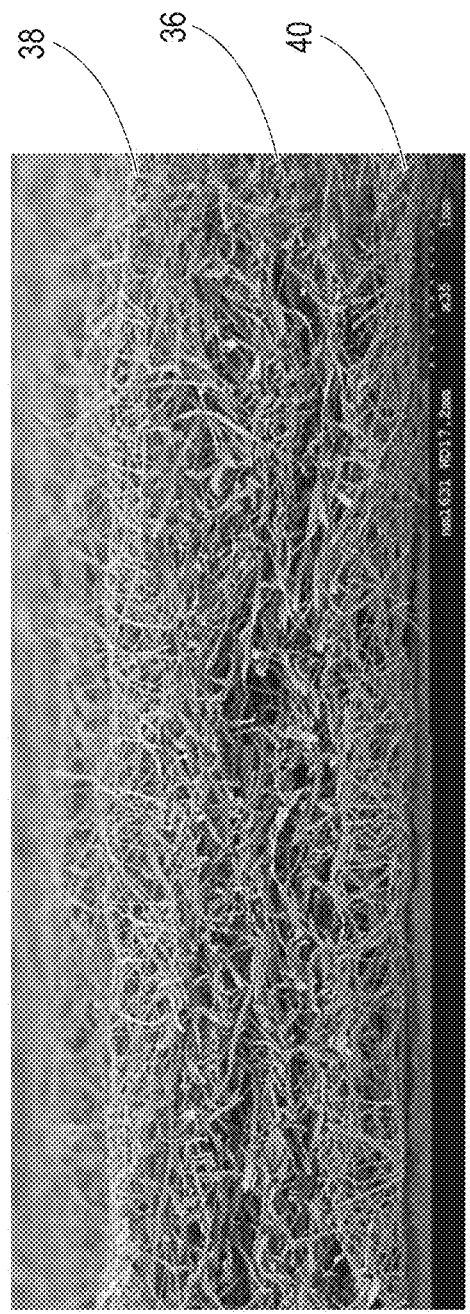
FIG. 6C is a scanning electron microscope image of cross-section of an example of a fibrous web structure depicting outer scrim layers formed of meltblown filaments sandwiching a core layer formed of a blend of pulp fibers and meltblown filaments.
Figure 6D:
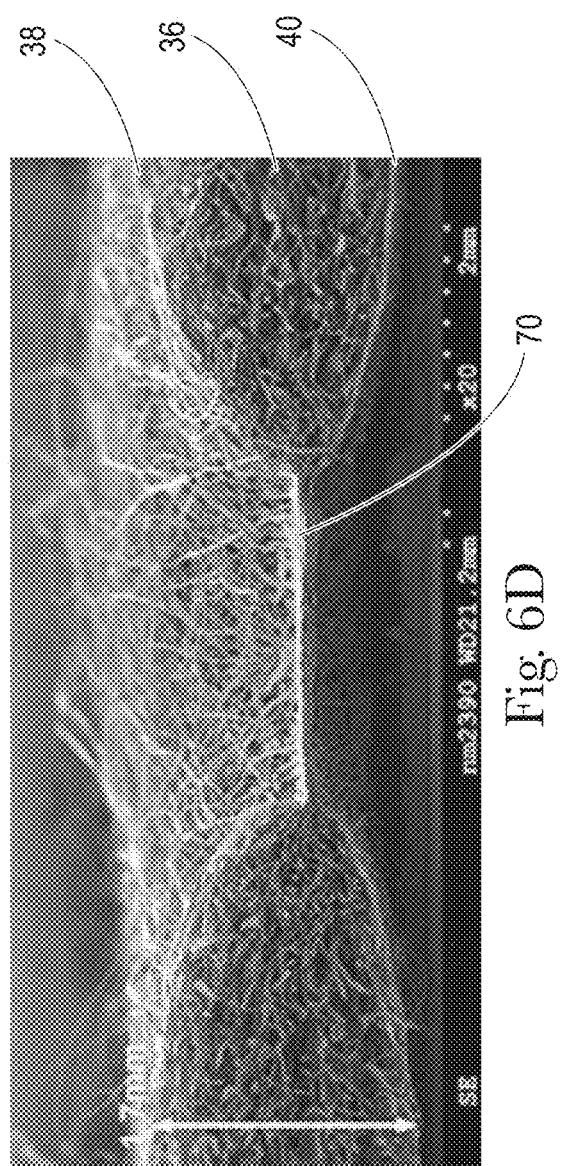
FIG. 6D is a scanning electron microscope image of cross-section of an example of a fibrous web structure depicting outer scrim layers formed of meltblown filaments sandwiching a core layer formed of a blend of pulp fibers and meltblown filaments, proximate a thermal bond.

FIGS. 6C and 6D are scanning electron microscope images of cross-sections of examples of a fibrous web structure depicting outer scrim layers 38, 40 formed of meltblown fibers, sandwiching a core layer 36 formed of a blend of pulp fibers and meltblown filaments. In FIGS. 6C and 6D it can be seen that the continuous filaments of the scrim layers 38, 40 are substantially finer than the pulp fibers in the core layer 36. When built up to a suitable basis weight, and in combination with a pattern of thermal bonds 70 binding the structure together in the z-direction, the scrim layers serve to help contain the relatively shorter and coarser pulp fibers within the structure. For the manufacturer, this desirably reduces release of pulp fibers into the plant environment in downstream processes involving the fibrous nonwoven structure, reducing contamination of equipment, among other benefits. For the consumer of a product made from the fibrous nonwoven structure, this desirably increases abrasion resistance of the product and reduces shedding of pulp fibers ("linting") from rubbing friction of the product during its use. Additionally, as has been found, surprisingly, inclusion of scrim layers imparts added tensile strength to the fibrous web structure, even when it constitutes a mere reallocation of a portion of the meltblown filaments from the core layer. Added tensile strength reduces incidents of tearing and puncturing of the structure, benefiting both the manufacturer in downstream processing, and the consumer in use of a product made from the structure.

It should also be noted that the presence of polymer filaments in the core layer 36 together with the presence of polymer filaments of like chemistry in the two outer scrim layers, facilitate formation of a thermal bond 70 at which the polymer material in the three layers can be brought together under heat and compression so that they at least partially fuse, as may be observed in FIG. 6D, thereby forming a robust bond through the web structure in the z-direction and holding the scrim layers to the structure. This helps maintain consolidation of the accumulated fibers and filaments, and enhances the structural integrity of the fibrous web structure. Further, it may be appreciated from FIG. 6D that the presence of scrim layers on a fibrous nonwoven web structure enables creation of a clearly, sharply defined thermal bond, which may enhance the visual appearance of thermal bond patterns that embody not only functional, but esthetic aspects.

As noted, it is believed that inclusion of meltspun, in one example meltspun and meltblown, polymer filaments in a co-formed fibrous web structure that is otherwise formed of cellulose or wood pulp fibers, as schematically illustrated in FIGS. 1 and 2 serves to enhance the tensile strength and wet structural integrity of the structure, making it particularly suitable for making wet wipes. Additionally, inclusion of outer scrim layers formed of meltspun, in one example meltspun and meltblown, polymer filaments as suggested and shown in FIGS. 6A-6C serves to help contain the shorter and coarser pulp fibers within the structure. Use of meltblown filaments to form outer scrim layers may be desirable because the relatively fine meltblown fibers form a scrim structure that is numerically dense (as compared to a structure of similar basis weight but formed of meltspun but not meltblown filaments), and therefore beneficial for containing fibers within the structure.

However, adding polymer filaments to pulp fibers in a fibrous web structure of a given basis weight (as occurs with the addition of outer scrim layers of meltblown polymer filaments) may compromise the capacity of the structure to absorb aqueous liquids, for many types of polymers typically suitable and desirable for melt-spinning. This is due to the fact that, while pulp fibers are typically naturally hydrophilic, the preferred polymer filaments, such as polypropylene filaments, are typically naturally hydrophobic.

What remains to be decided, then, is an appropriate combination of weight percent pulp fiber content vs. filament content, with an appropriate allocation of meltspun/meltblown filament content to the scrim layers.

For the liquid absorbency performance desired for a wet wipe product it may be desired that the entire fibrous web structure be formed of at least 50 percent, more preferably at least 60 percent, and still more preferably at least 65 percent, by weight pulp fibers. Conversely, to achieve desired tensile strength and wet structural integrity, it may be desired that the entire fibrous web structure include at least 10 percent, at least 20 percent, or at least 25 percent, by weight polymer filaments. Thus, in some examples it may be preferred that the fibrous web structure be formed of 50 to 90 percent by weight pulp fibers, or 60 to 85 percent by weight pulp fibers, or even 65 to 85 percent by weight pulp fiber. Correspondingly, in such examples the fibrous web structure may comprise 10 to 50 percent by weight polymer filaments, or 15 to 40 percent by weight polymer filaments, or even 15 to 35 percent by weight polymer filaments, respectively.

Referring to FIGS. 6A-6D, what remains to be further decided is an appropriate allocation of polymer filaments between the inner or "core" layer(s) 36 and the outer scrim layers 38, 40 for purposes of best maximizing or appropriately balancing qualities such as drape or flexibility, surface roughness, tactile feel, opacity and tensile strength. Within the contemplation of a structure as schematically illustrated in FIG. 6A, any quantity ranging from a very small portion, to nearly all, of the polymer filaments in the structure, may be allocated to the scrim layers. However, it was not expected or predicted that, within the ranges of pulp and filament content set forth in the preceding paragraph, reallocating a portion of polymer filaments from the inner core layer(s) to outer scrim layers of a fibrous web structure would have any substantial effect on properties such as tensile strength, opacity or flexibility of the structure, since it was believed that a mere reallocation from core to scrim layers theoretically does not increase or decrease the number of filaments per unit surface area of the structure.

Figure 12:
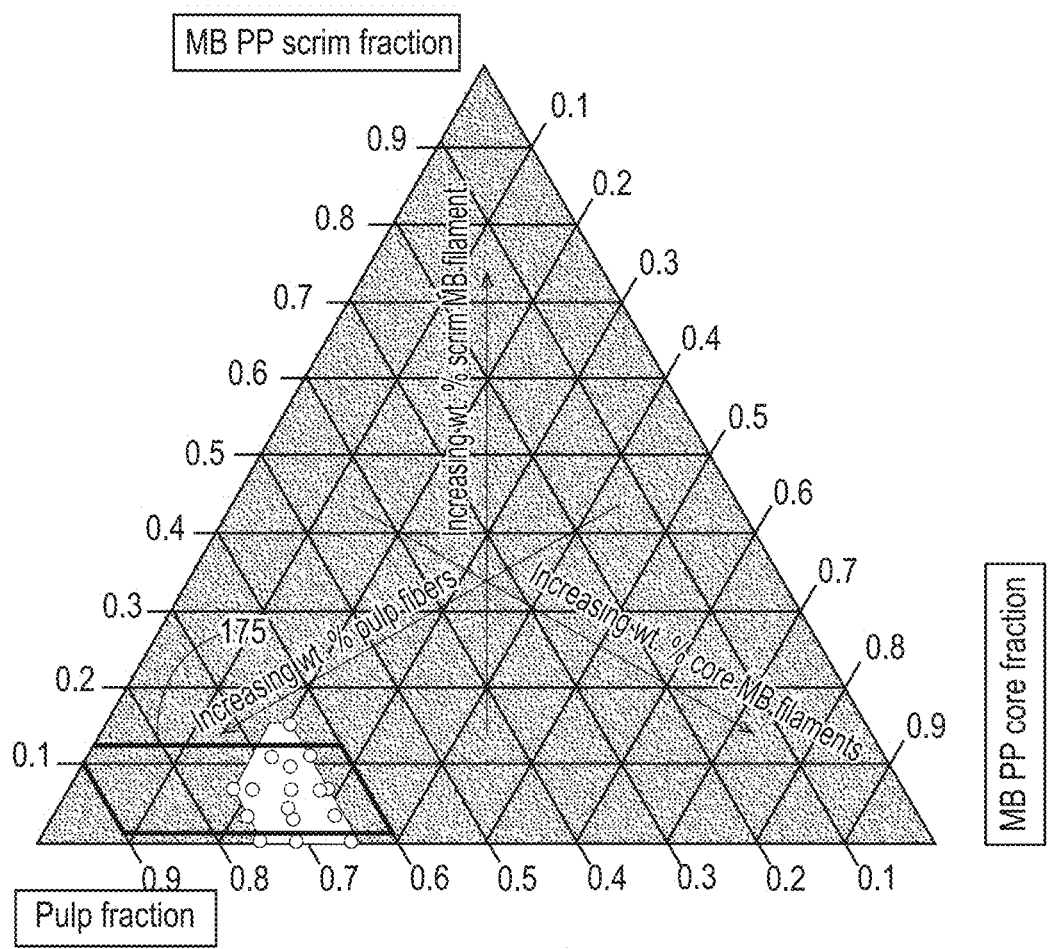
FIG. 12 is a ternary plot of the fraction of pulp, the fraction of meltblown polypropylene filaments present in two scrim layers, and the fraction of meltblown polypropylene filaments in the core layer, of the total weight, of each of seventeen samples of fibrous web structures comprising pulp fibers and meltblown polypropylene filaments.
Figure 13:
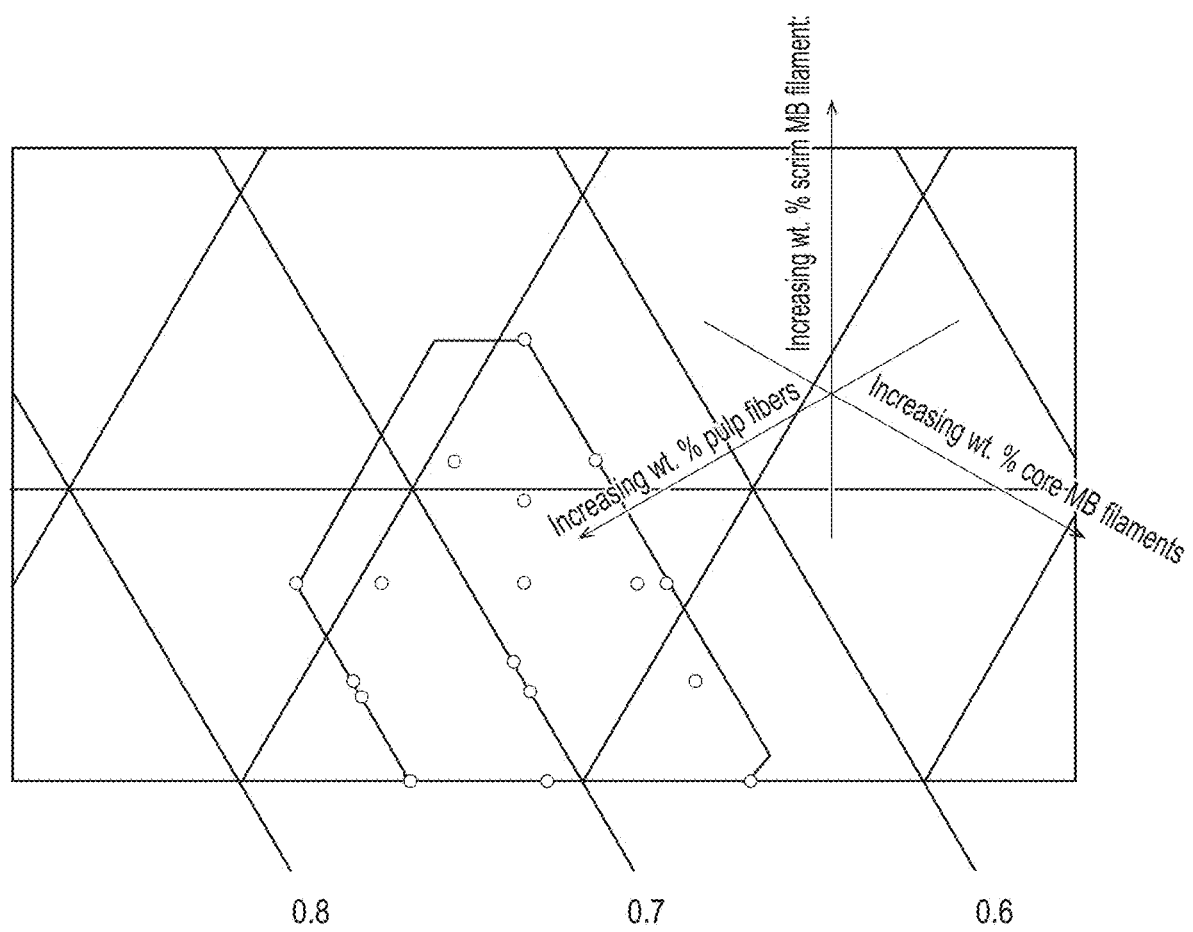
FIG. 13 is an enlarged view of the portion of the plot of FIG. 12 occupied by data points.

In an attempt to determine appropriate combinations of pulp content and allocation of filaments between core and scrim layers, however, seventeen variants of a three layer (scrim-core-scrim) fibrous nonwoven web structure such as schematically illustrated in FIG. 6A, of basis weights of about 55 gsm and 60 gsm, and comprising from about 65 percent to about 75 percent by weight SSK pulp fibers, and the remainder meltblown polypropylene filaments, were manufactured. The two scrim layers had approximately equal basis weights, for each variant. The variants had the weight fractions of SSK pulp fiber and allocations of meltblown polypropylene filaments reflected in the data points in the ternary plot shown in FIGS. 12 and 13. (The values shown on the axes of the ternary plot of FIG. 12 may be converted to weight percentages by multiplying them ×100%) The weight fraction meltblown of polypropylene filament content in a single outer scrim layer (i.e., on one side of the structure) for any particular variant, is approximately the value shown in the ternary plot, divided by 2. (The three-axis "compass" appearing in FIG. 12 shows, respectively, the direction of increasing weight fraction of pulp fibers in the structure, the direction of increasing weight fraction of meltblown (MB) polymer filaments in the scrim layers combined, and the direction of increasing weight fraction of meltblown (MB) polymer filaments in the core layer. This "compass" is also reproduced for reference in FIGS. 13 and 14A-14I.)

Figure 14A:
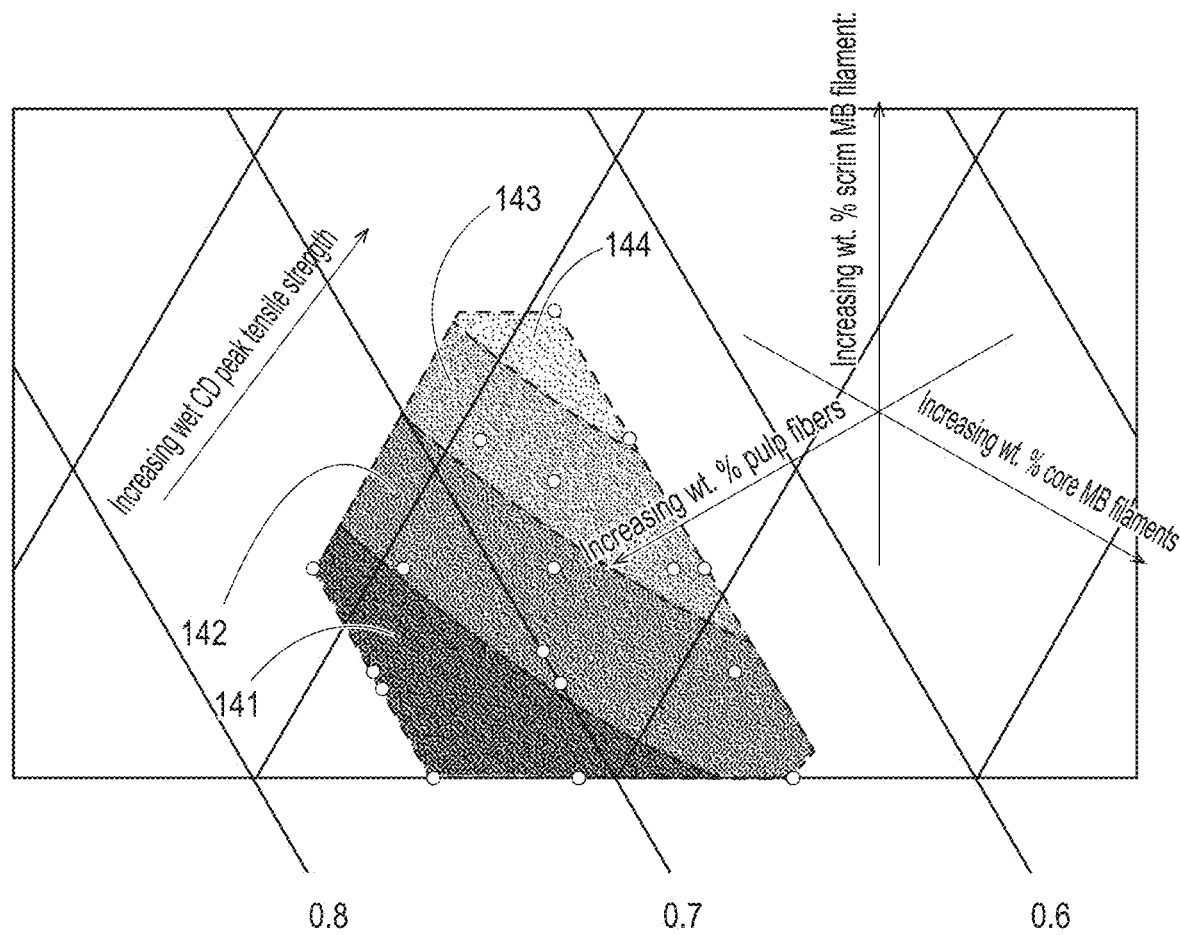
FIG. 14A is a view of the portion of the plot shown in FIG. 13, overlaid with shaded bands reflecting application of a predictive model developed from the data points, predicting wet cross direction peak tensile strength according to the fraction of pulp fibers, the fraction of meltblown polypropylene filaments in scrim layers, and the fraction of meltblown polypropylene filaments in a core layer, of a fibrous web structure.
Figure 14B:
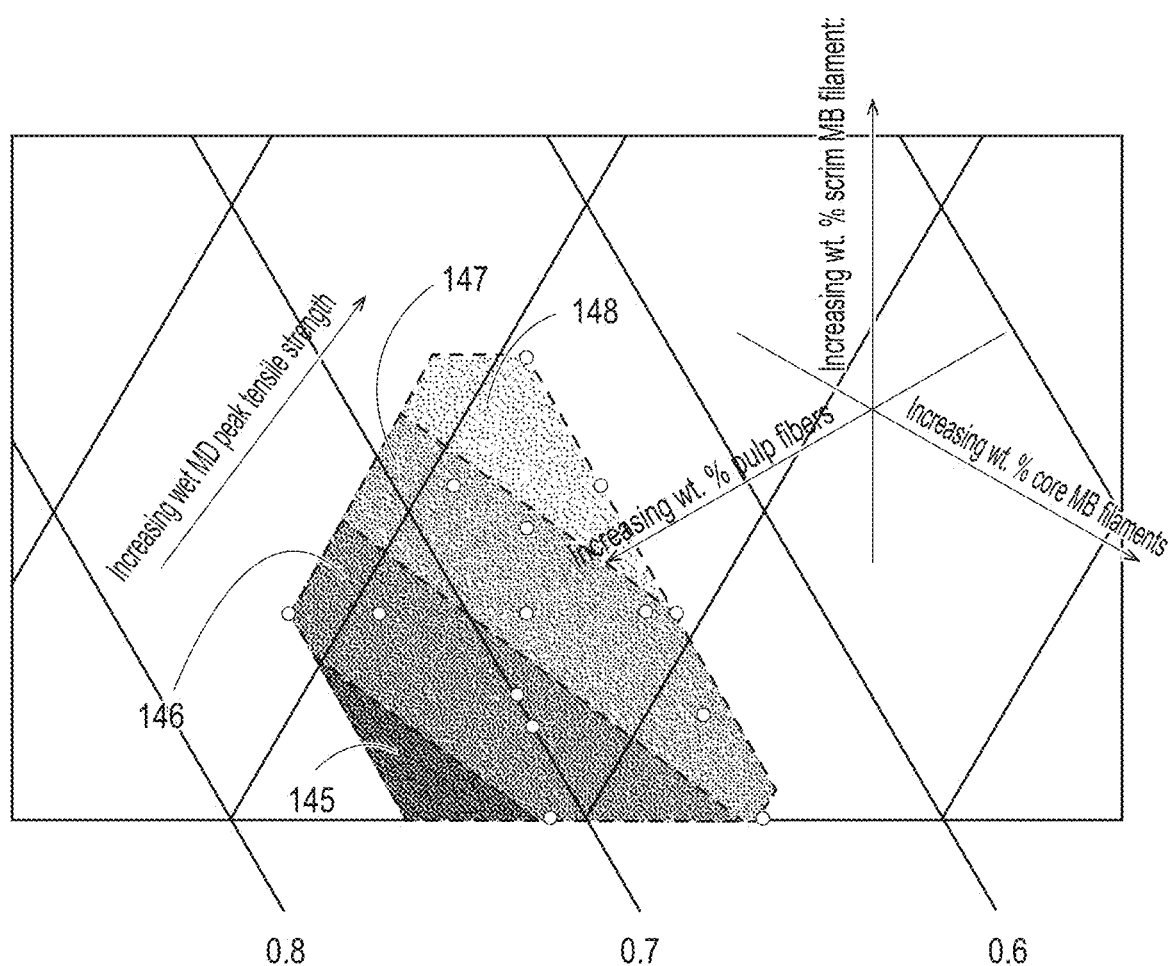
FIG. 14B is a view of the portion of the plot shown in FIG. 13, overlaid with shaded bands reflecting application of a predictive model developed from the data points, predicting wet machine direction peak tensile strength according to the fraction of pulp fibers, the fraction of meltblown polypropylene filaments in scrim layers, and the fraction of meltblown polypropylene filaments in a core layer, of a fibrous web structure.
Figure 14C:
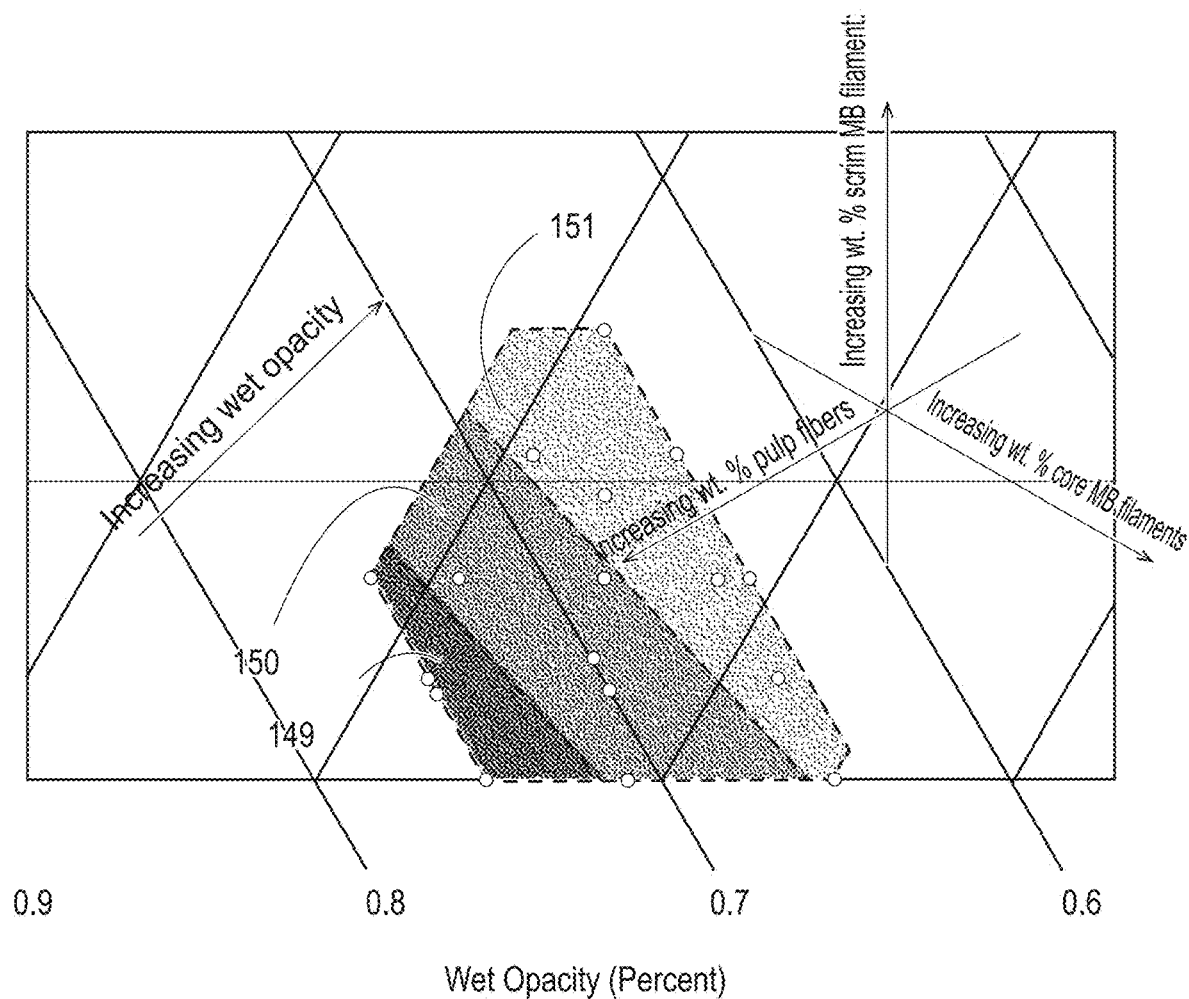
FIG. 14C is a view of the portion of the plot shown in FIG. 13, overlaid with shaded bands reflecting application of a predictive model developed from the data points, predicting wet opacity according to the fraction of pulp fibers, the fraction of meltblown polypropylene filaments in scrim layers, and the fraction of meltblown polypropylene filaments in a core layer, of a fibrous web structure with a basis weight of 55 gsm.
Figure 14D:
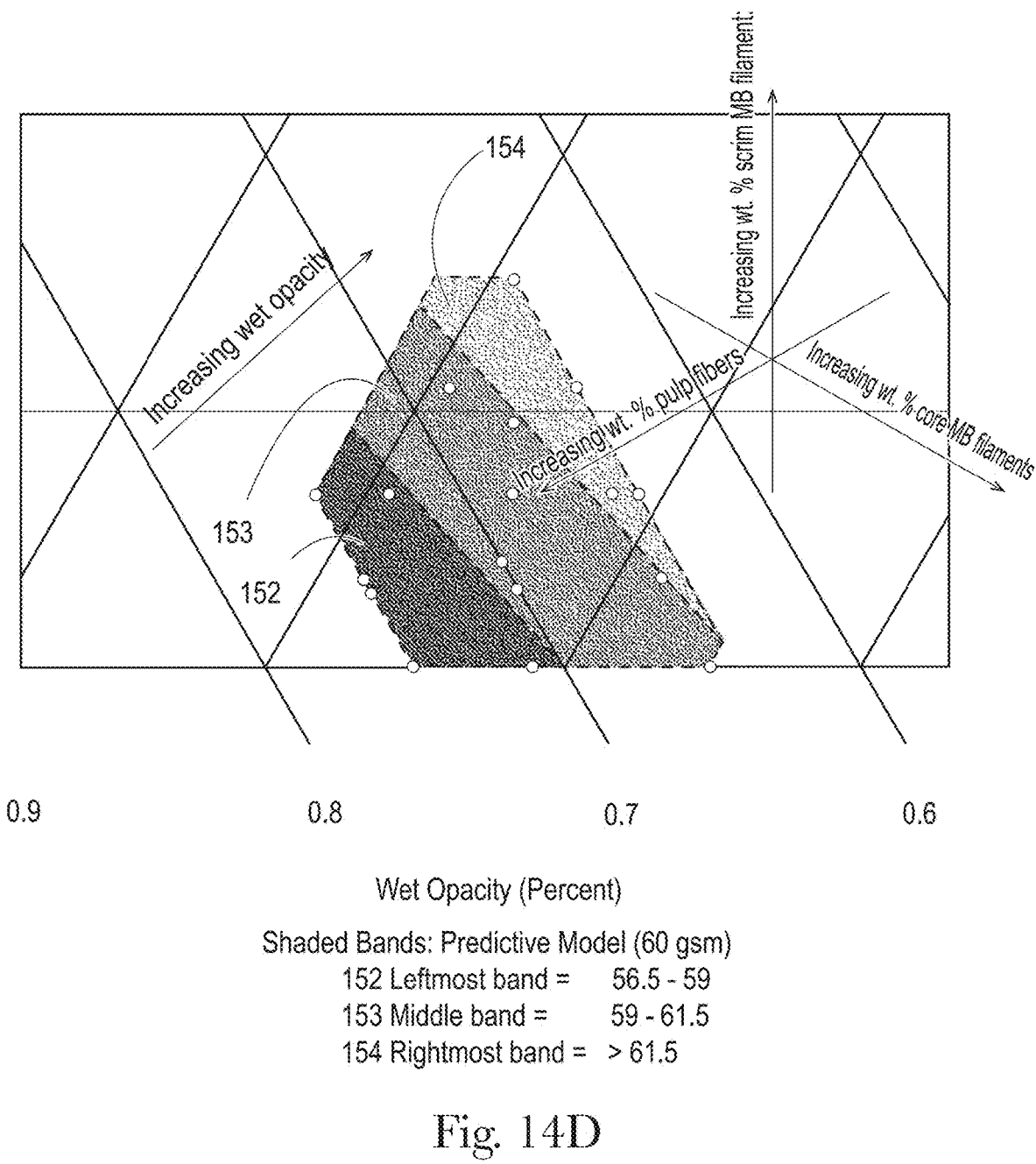
FIG. 14D is a view of the portion of the plot shown in FIG. 13, overlaid with shaded bands reflecting application of a predictive model developed from the data points, predicting wet opacity according to the fraction of pulp fibers, the fraction of meltblown polypropylene filaments in scrim layers, and the fraction of meltblown polypropylene filaments in a core layer, of a fibrous web structure with a basis weight of 60 gsm.
Figure 14E:
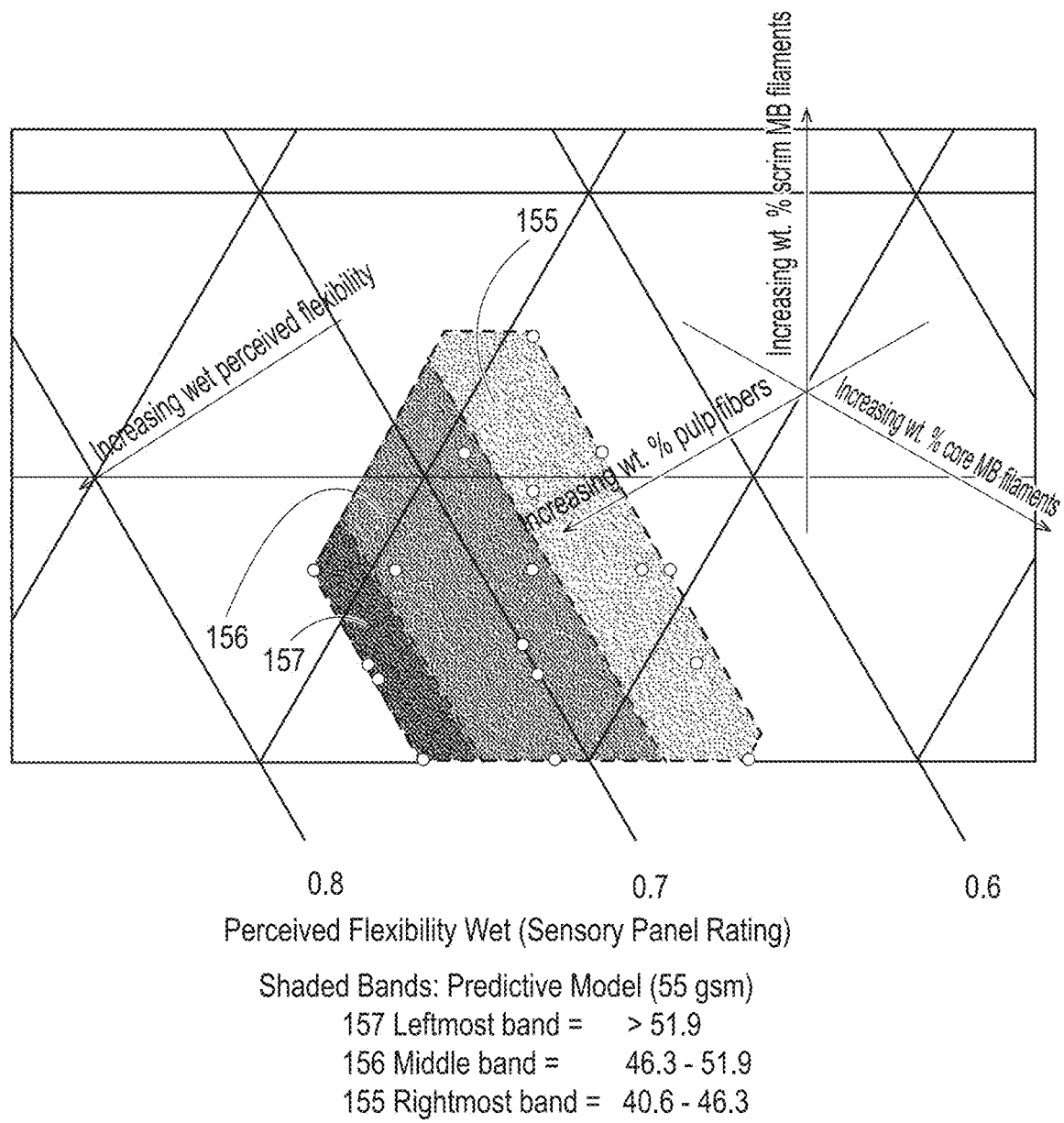
FIG. 14E is a view of the portion of the plot shown in FIG. 13, overlaid with shaded bands reflecting application of a predictive model developed from the data points, predicting perceived flexibility (wet) according to the fraction of pulp fibers, the fraction of meltblown polypropylene filaments in scrim layers, and the fraction of meltblown polypropylene filaments in a core layer, of a fibrous web structure having a basis weight of 55 gsm.

In a first assessment, wet cross direction and machine direction tensile strength of these seventeen variants was measured and recorded. A regression analysis was applied to the data and yielded a formula. The formula predicts that adding meltblown polypropylene filaments to the overall structure, enhances wet tensile strength. Surprisingly, however, the formula also predicts, generally, that increasing allocation of the added filaments from the core layer to the scrim layers by even a small amount appears to dramatically impact wet tensile strength of the fibrous nonwoven structure, with tensile strength increasing generally as more filaments are allocated from the core layer to the scrim layers—within the weight ratios of wood pulp fibers to polymer filaments contemplated. This effect is illustrated in FIGS. 14A and 14B, in which wet cross direction and machine direction peak tensile strength of the structure is predicted to increase dramatically as the weight ratio of meltblown polymer filaments to pulp fibers is increased, and as the allocation of those meltblown polymer filaments is shifted from core to scrim layers. This is indicated by the shaded bands marked 141-144 in FIG. 14A, and shaded bands marked 145-148 in FIG. 14B.

Since this effect was not predicted, the reasons for it are not currently well understood. Without intending to be bound by theory, it is hypothesized that higher numeric density of meltblown filaments (i.e., greater consolidation in the z-direction) may contribute to adding tensile strength to a structure formed of the filaments, while lower numeric density of meltblown filaments within the same space (such as when separated in the z-direction by interspersed fibers) may reduce tensile strength. Regardless, it was predicted that consumers of products made from the structure, such as baby wipes, would prefer comparatively greater tensile strength in the structure. This is due to the fact that comparatively greater tensile provides comparatively greater resistance to tearing and puncturing in dispensation and use, and the fact that tearing or puncturing during dispensation and/or use are undesirable failures for a baby wipe. This prediction is also supported by results of consumer research, which suggest that consumers tend to prefer comparatively more strength and tear resistance in a baby wipe.

In a second assessment, wet opacity of the seventeen variants was measured and recorded. Another regression analysis was applied to the data and yielded a formula. The formula predicted that opacity increases as basis weight of the fibrous web structure is increased; compare FIGS. 14C and 14D. This in itself was not surprising, since comparatively greater basis weight equates with a comparatively greater number of fibers and filaments per unit surface area, which would be expected to be available to block or diffuse comparatively more light directed orthogonally at one surface. Surprisingly, however, the formula also predicts that opacity of the fibrous nonwoven structure generally increases as more filaments are allocated from the core layer to the scrim layers, within the weight ratios of wood pulp fibers to polymer filaments contemplated. This effect is also illustrated by the shaded bands marked 149-151, and 152-154, respectively, in FIGS. 14C and 14D.

Since the overall numbers of fibers and filaments present is generally not increased by a mere allocation of filaments from core to scrim layers, the reasons for this effect are not currently well understood. However, it was predicted that consumers of products made from the structure, such as baby wipes, would prefer comparatively greater opacity, since comparatively greater opacity equates with comparatively less translucency, making the wipe look more substantial and as if it better creates a physical barrier between the user's hand and soil (e.g. fecal matter) that the wipe is used to clean away from the baby's skin.

In another assessment, the seventeen variants were presented to a panel of human respondents, who were asked to evaluate the structure samples and rate them according to the extent to which they subjectively deemed them flexible. A subjective scoring system was used. Another regression analysis was applied to the data collected, and yielded a formula that is reflected in FIGS. 14E and 14F. Generally, the formula predicts that relatively higher pulp content and relatively lower allocation of meltblown filaments to the scrim layers results in a relatively higher flexibility rating, and vice versa, as reflected in shaded bands 155-157, and 158-160, respectively, in FIGS. 14E and 14F.

Consumer preferences concerning flexibility are complex and not currently thoroughly understood. Without intending to be bound by theory, it is believed that some consumers may prefer a comparatively more flexible structure, perceiving it to be, for example, more soft and luxurious, while others may prefer a comparatively stiffer structure, perceiving it to be, for example, more robust and substantial.

In still another assessment, the seventeen variants were presented to the panel of human respondents, who were asked to evaluate the structure samples and rate them according to their perceptions of surface roughness. A subjective scoring system was used. Another regression analysis was applied to the data collected, and yielded a formula that is reflected in FIG. 14G. Generally, the formula predicts that relatively lower allocation of meltblown filaments to the scrim layers results in a relatively higher surface roughness rating, and vice versa, as reflected by shaded bands 161-164 in FIG. 14G.

Consumer preferences concerning surface roughness are also somewhat complex and not currently thoroughly understood. Without intending to be bound by theory, it is believed that some consumers may prefer a more rough-feeling structure (e.g., more like a paper towel), perceiving it to be, for example, more effective at sweeping, capturing and removing soil from skin, while others may prefer more smooth-feeling structure, perceiving it to be, for example, more gentle to skin and/or more soft and luxurious.

Although they provide some guidance concerning how to maximize particular properties such as tensile strength and opacity, the assessments described above do not appear to provide any certain guidance, prediction or expectation as to how to select a combination of weight percent pulp fiber content vs. meltblown filament content, and an allocation of meltblown filament content between the core layer and the scrim layers, that will be most pleasing to consumers of wet wipes such as baby wipes.

Figure 14F:
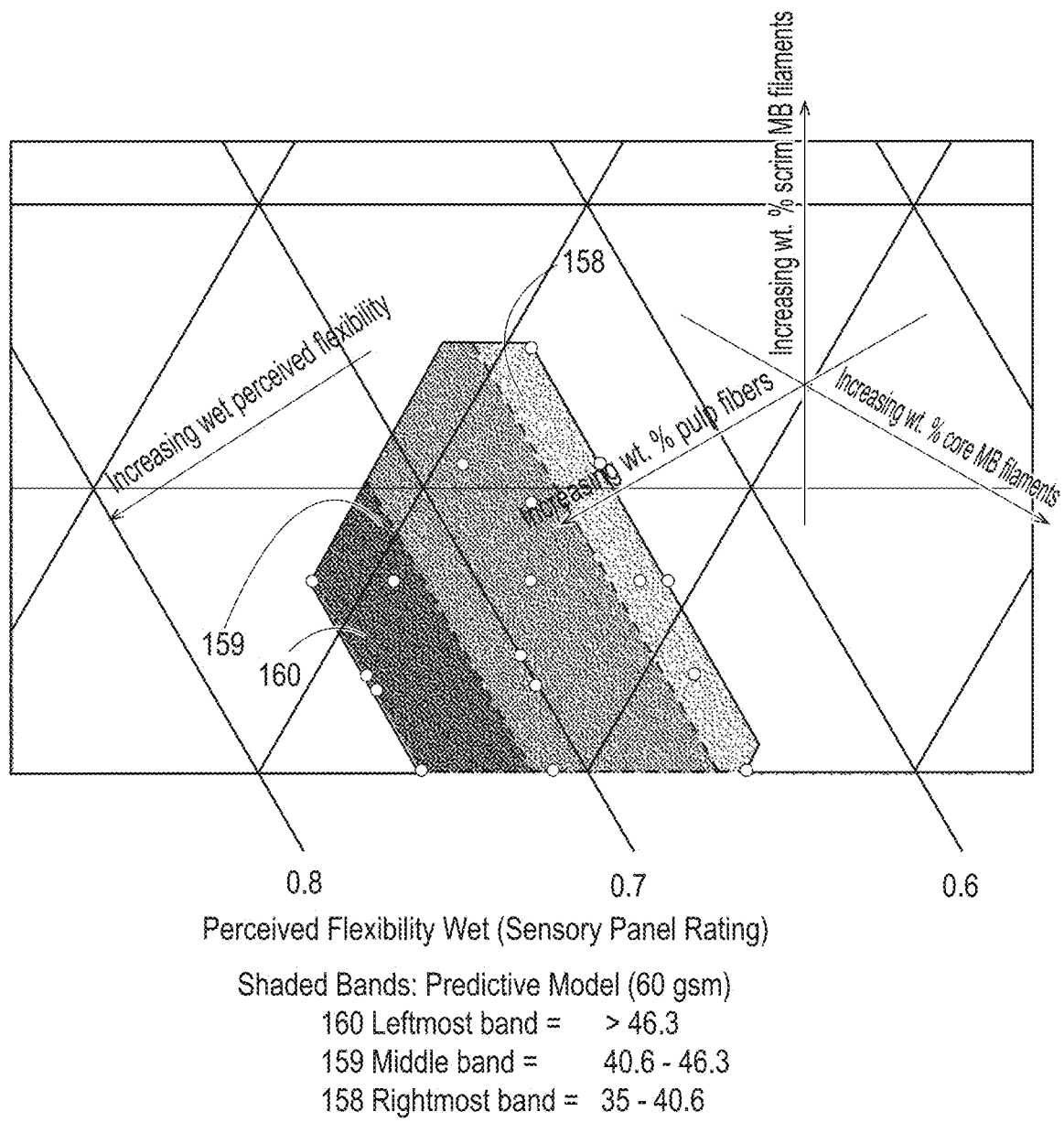
FIG. 14F is a view of the portion of the plot shown in FIG. 13, overlaid with shaded bands reflecting application of a predictive model developed from the data points, predicting perceived flexibility (wet) according to the fraction of pulp fibers, the fraction of meltblown polypropylene filaments in scrim layers, and the fraction of meltblown polypropylene filaments in a core layer, of a fibrous web structure having a basis weight of 60 gsm.
Figure 14G:
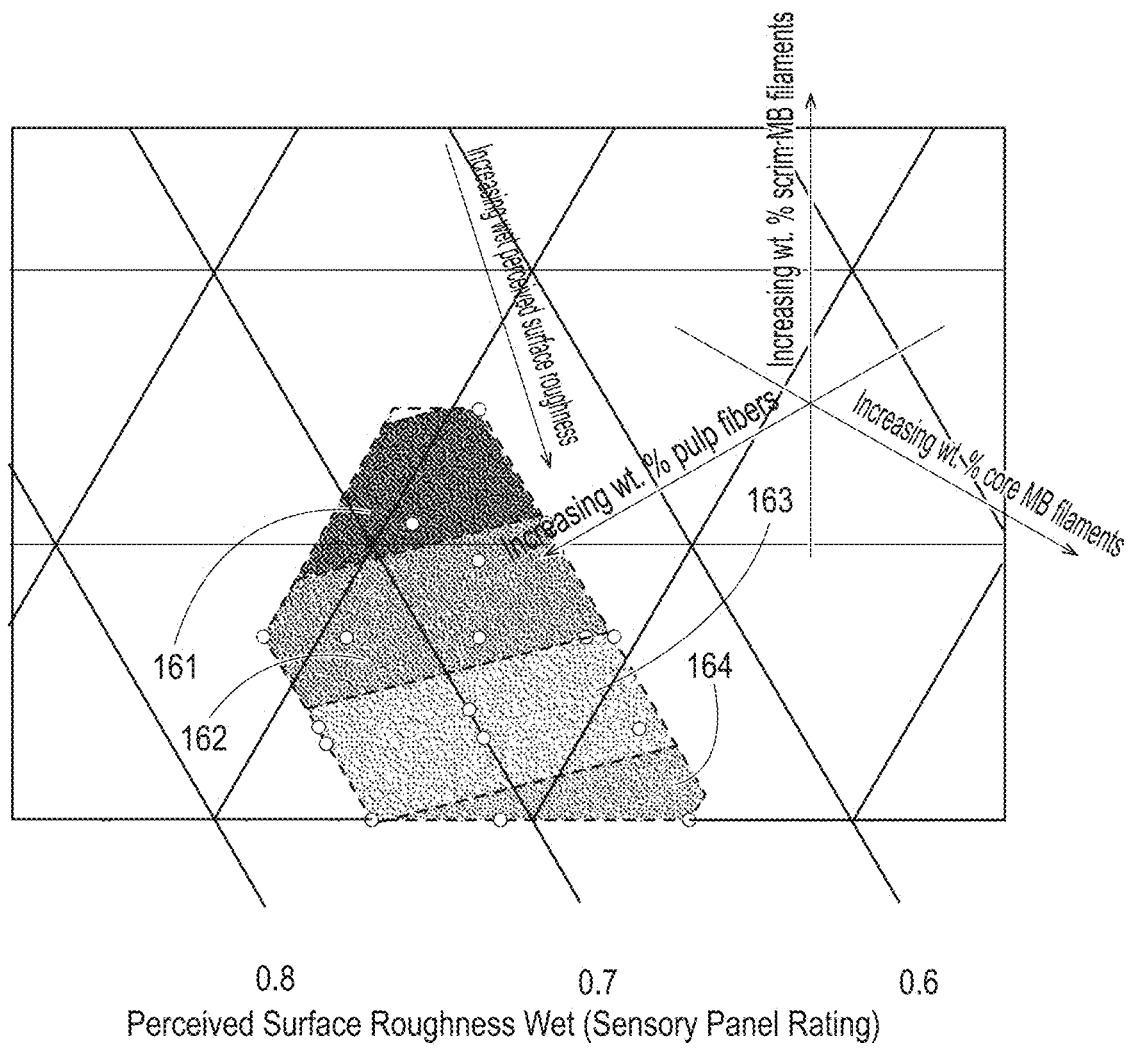
FIG. 14G is a view of the portion of the plot shown in FIG. 13, overlaid with shaded bands reflecting application of a predictive model developed from the data points, predicting perceived surface roughness (wet) according to the fraction of pulp fibers, the fraction of meltblown polypropylene filaments in scrim layers, and the fraction of meltblown polypropylene filaments in a core layer, of a fibrous web structure.

Samples of the seventeen variants that had been converted to wet wipes were presented to another panel of consumer respondents, who were asked to evaluate the wipes samples and rate them according to the extent to which they would prefer to purchase them as consumers. A subjective scoring system was used. Another regression analysis was applied to the data collected, and yielded a formula that, surprisingly, showed little correlation with the formulas for tensile strength and opacity. There was little correlation between the predicted most preferred higher tensile strength, the predicted most preferred higher opacity, and the most preferred consumer preference, for structures with varying allocations of meltblown polymer filaments to the scrim layers. Rather, as reflected by respective shaded bands 165-169 and 170-174 in FIGS. 14H and 14I, the Consumer Preference Indication formula suggests that the strongest consumer preference falls within a narrow band of allocation of meltblown polymer filaments to the outer scrim layers, from about 1.0 percent by weight of the total fibrous web structure allocated to the scrim layers, to about 13 percent by weight of the total fibrous web structure, of meltblown polymer filaments allocated to the scrim layers, for, e.g., a 60 gsm fibrous web structure (FIG. 14F). At allocations of meltblown filament content lower than about 1.0 percent by weight of the structure to the scrim layers, and higher than about 13 percent, consumer preference falls off sharply, for reasons currently not thoroughly understood.

A model derived from the regression analysis enables a prediction of consumer preference from the ranges of the basis weights and proportions of pulp fibers of the samples tested. From the analysis, it is preferred that the Consumer Preference Indication for a fibrous nonwoven structure be greater than 0.0, more preferably 1.0 or more, still more preferably 1.75 or more, and still more preferably 2.25 or more, where Consumer preference Indication is calculated according to the following equation:

$$CPI=(BW\times0.06232)-6.00192A-6.84371B-3.95686C+13.67992AB+7.12309BC+2,$$

where $A=[(\text{Weight fraction pulp content})-0.64167]/0.175;$
$B=(\text{Weight fraction meltblown filaments in scrim layers})/0.175;$
$C=[(\text{Weight fraction meltblown filaments in core layer})-0.18333]/0.175;$ and
$BW=$basis weight of the fibrous web structure in gsm.

Thus, as one example, according to the model described above and the description herein, a fibrous web structure having a basis weight of 60 gsm and the following composition will be a within the range of consumer preference indicated by CPI as set forth above:
- 17.40 gsm meltblown polypropylene filaments in middle/core layer;
- 39.00 gsm SSK pulp fibers in middle/core layer;
- 3.60 gsm meltblown polypropylene filaments in outer/scrim layers together (approximately 1.8 gsm in each); and
- bond area percentage about 6.2%.

From the values above, the example structure will have 65.0 percent by weight pulp fibers, 6.00 percent by weight meltblown polymer filaments in the two scrim layers together, and 29.0 percent by weight meltbown polymer filaments in the middle/core layer, and will have a CPI of 2.4071 according to the above model, indicating a consumer-preferred structure.

In contrast, if the above example is modified such that 3.00 gsm is additionally allocated from the core layer to each scrim layer (allocating a total of 9.60 gsm to the scrim layers together, or 4.80 gsm to each), the structure would have 16.0 percent by weight meltblown polymer filaments in the two scrim layers, and 19.0 percent by weight meltbown polymer filaments in the middle/core layer, and will have a CPI of about −0.1108, indicating a structure that is outside the consumer-preferred range in which the CPI is greater than 0.

It may be recognized that a web formed of meltblown polymer filaments to a basis weight of 4.8 gsm or less, by itself, is extremely thin and sheer, and barely tactilely perceptible when held in the hands. This illustrates the surprising sensitivity of consumer preference to allocation of meltblown filaments to the scrim layers, according to the model. It may be appreciated from the foregoing that consumer preferences are often elusive to prediction and that more than routine experimentation is necessary to discover them and then harmonize them with manufacturer preferences for features such as material strength, manufacturing cost and efficiency. The above-described formula for achieving a CPI greater than 0, more preferably 1, still more preferably 2, showed little correlation with the formulas that indicate maximization of properties such as tensile strength, opacity, surface roughness and flexibility with respect to choosing a combination of pulp fiber content, meltblown filament content and allocation of meltblown filaments between core and scrim layers.

Results of further consumer testing have suggested that extrapolation from the model above may yield ranges of consumer-preferred allocations of meltblown filaments for higher and lower proportionate pulp content structures than the variants made, tested and shown and plotted in the ternary plots of FIGS. 12-14I. This extrapolation is reflected by the dotted-line parallelogram 175 drawn on the ternary plot of FIG. 12. Extrapolation indicates a preferred weight percent pulp content of 60% to 90%, combined with a preferred meltblown filament weight percent content in the scrim layers (combined) of 1.0% to 13%.

Based on the foregoing, examples of a fibrous nonwoven structure are contemplated having a combination of the following features:
- Basis weight: 40 gsm to 100 gsm, more preferably 50 gsm to 90 gsm, more preferably 55 to 85 gsm, and still more preferably 60 gsm to 80 gsm, or alternatively, any combination of the lower and upper values of the above ranges, e.g., 40-85 gsm, 40-80 gsm, etc.;
- Composition: 60 to 90 percent by weight cellulose fibers, preferably wood pulp fibers, and more preferably a blend of softwood and hardwood fibers, and still more preferably a blend of SSK fibers and hardwood fibers, for example, *Eucalyptus* fibers; and 10 to 40 percent by weight meltblown polymer filaments, more preferably meltblown polyolefin filaments, and still more preferably meltblown filaments formed predominately of polypropylene; and
  - (a) From about 1.0 weight percent to about 13.0 weight percent of the structure, of meltblown filaments in scrim layers, or more preferably, from about 3 weight percent to about 11 weight percent of the structure, of meltblown filaments in scrim layers, still more preferably, from about 5 weight percent to about 9 weight percent of the structure, of meltblown filaments in scrim layers, or alternatively,
  - (b) allocation of meltblown filaments between core layer(s) and scrim layers such that the CPI according to the model above is greater than 0, more preferably 1.0 or greater, still more preferably 1.75 or greater, and even more preferably 2.25 or greater,
    - where alternative (a) or (b) is combined with a basis weight for at least one scrim layer of at least 0.1 gsm and a combined basis weight that is equal to or less than 13 weight percent of the structure; or alternatively,
  - (c) the basis weight of a single scrim layer (i.e., on one side of the structure) is kept within a range of from 0.1 gsm to less than 3.0 gsm.

Figure 14H:
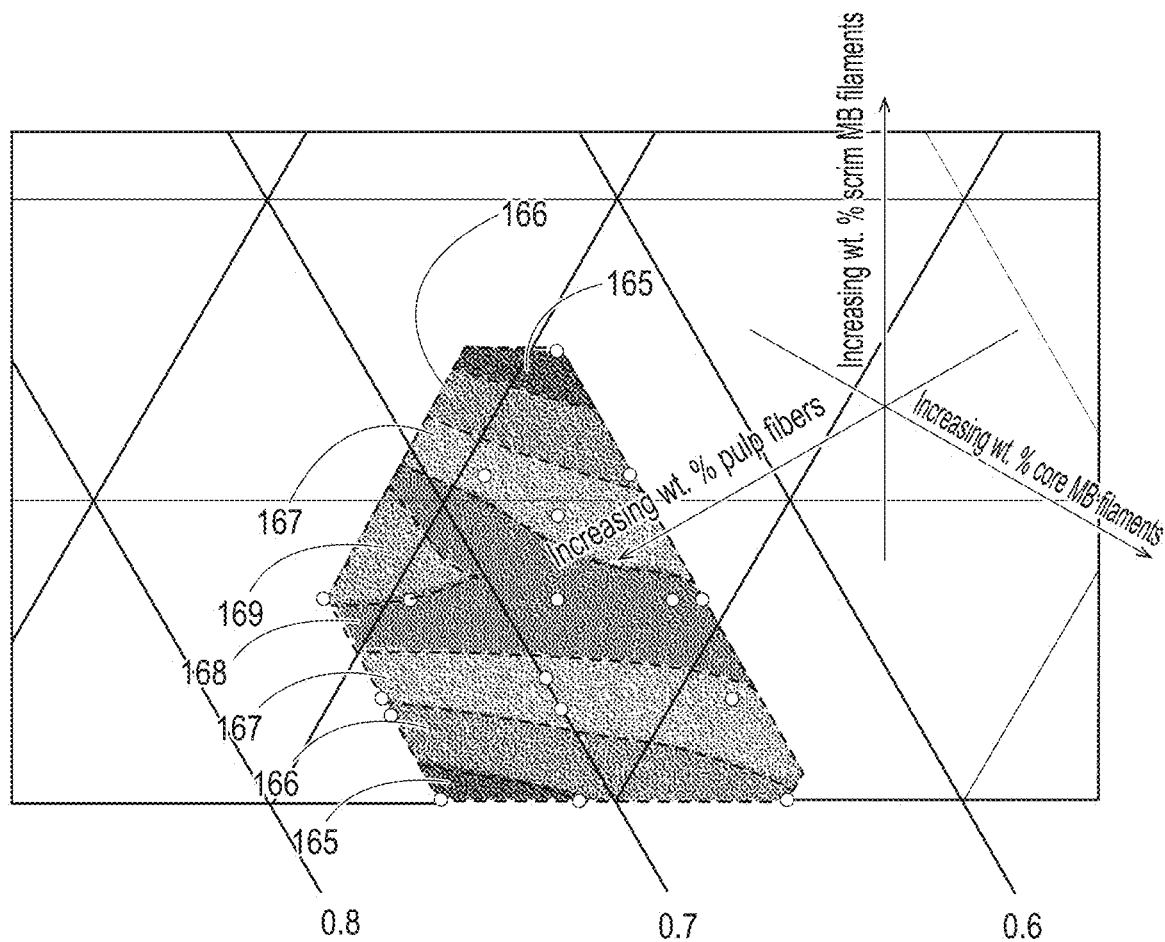
FIG. 14H is a view of the portion of the plot shown in FIG. 13, overlaid with shaded bands reflecting application of a predictive model developed from the data points, predicting Consumer Preference Indication (CPI) (wet) according to the fraction of pulp fibers, the fraction of meltblown polypropylene filaments in scrim layers, and the fraction of meltblown polypropylene filaments in a core layer, of a fibrous web structure having a basis weight of 55 gsm.
Figure 14:
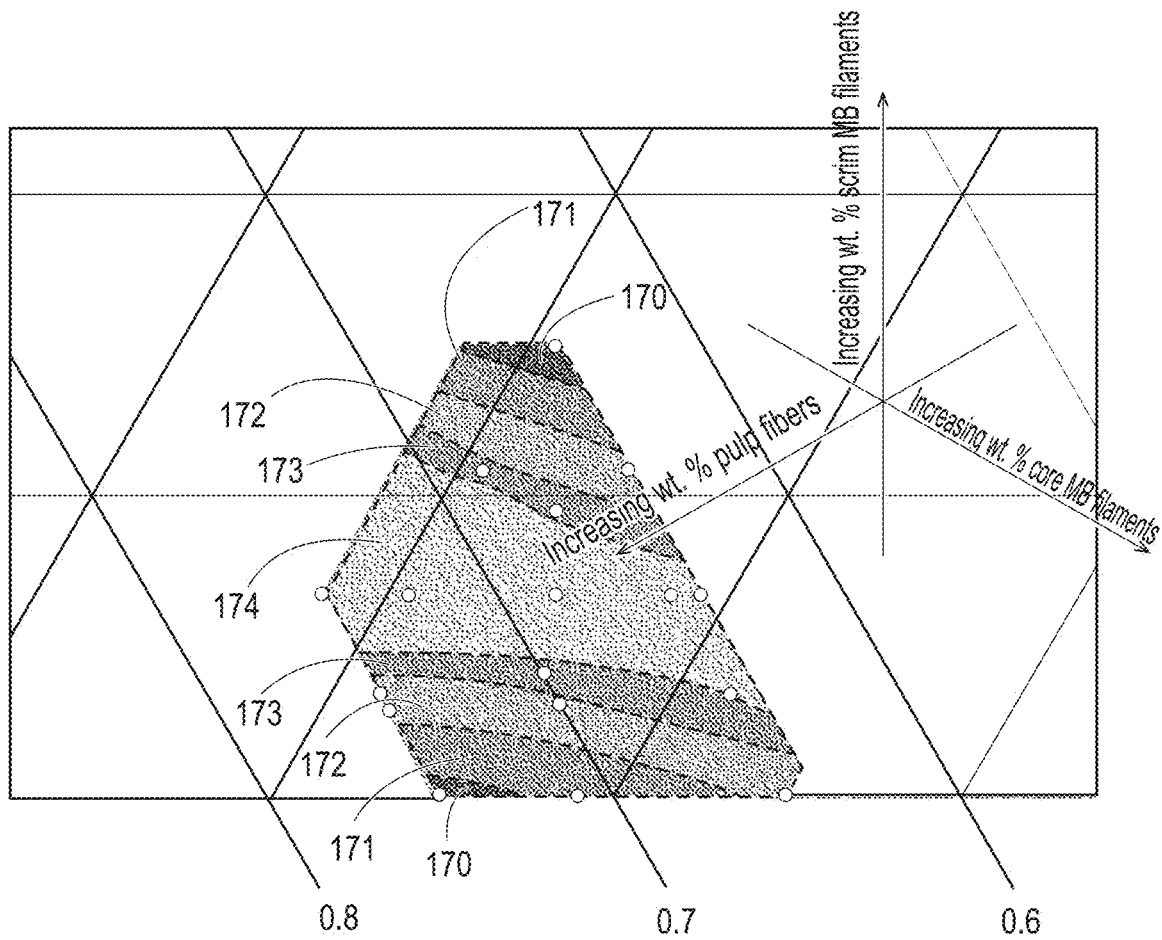
FIG. 14I is a view of the portion of the plot shown in FIG. 13, overlaid with shaded bands reflecting application of a predictive model developed from the data points, predicting Consumer Preference Indication (CPI) (wet) according to the fraction of pulp fibers, the fraction of meltblown polypropylene filaments in scrim layers, and the fraction of meltblown polypropylene filaments in a core layer, of a fibrous web structure having a basis weight of 60 gsm.

In hindsight of this research and analysis it appears that consumers will prefer a wet wipe cut from a fibrous web material having at least some of the total meltblown polymer fiber weight content allocated to scrim layers, but that that preference is very sensitive and falls off sharply when the allocation of meltblown filaments to the scrim layers strays above or below a relatively narrow band, as suggested in FIGS. 14H and 14I. Expressed differently, the benefits of scrim layers on a fibrous web structure are believed to be best realized, from a consumer preference perspective, when included, but kept to low basis weights within the ranges described herein.

The amount of meltblown polymer filaments allocated to the two scrim layers may be divided approximately equally, or may be divided unequally. For example, it may be desired that the two sides of the fibrous nonwoven structure have different feel or surface characteristics, for example, that one side have a more rough or higher-friction feel, and the other side have a more smooth or slick, lower-friction feel. To accomplish such difference, the scrim layer on one side may be imparted with a lower basis weight of, for example, from 0.1 gsm to 1.4 gsm, or to 1.0 gsm, or even to 0.6 gsm. Correspondingly, the scrim layer on the other side may be imparted with a higher basis weight of, for example, from 0.6 gsm to 3.0 gsm, or from 0.8 gsm to 2.8 gsm, or even from 1.0 gsm to 2.6 gsm. In order to provide the pulp fiber containment benefit of a scrim layer, however, as noted above, it may be desired that the basis weight of either scrim layer and preferably both scrim layers be at least 0.1 gsm, more preferably at least 0.2 gsm, or even more preferably at least 0.3 gsm. For example, for a fibrous nonwoven structure having a basis weight of, e.g., 60 gsm, this means that it may be desired that the weight percentage of either or preferably both scrim layers be at least 0.17%, or 0.34% combined.

The basis weight of the fibrous web structure, the overall weight percent pulp content vs. meltblown filament content, and the allocation of meltblown filaments between core layer(s) and scrim layers may be adjusted and regulated by design, adjustment and regulation of the speeds and/or feed rates to components that introduce the materials in the manufacturing line, including the components that separate and feed the pulp fibers and entrain them in airstream(s), the banks of filament spinnerets, the forming belt, etc.

From FIGS. 6C and 6D it may be appreciated that inclusion of scrim layers formed of meltblown polymer fibers, as described above, on the fibrous web structure, may impart a smoother-feeling texture to the outer surfaces of the structure as a result of the fine polymer filament scrim layers covering the rougher-feeling pulp fibers in the core layer. Without intending to be bound by theory, it is believed that, for some wipes consumers, this may not be desirable because it may be perceived to reduce surface roughness and reflect negatively on the cleaning efficacy of the wipe.

For purposes such as those described herein, pulp fiber is generally provided in the market in the form of air dry pulp in compressed, consolidated sheets ("dry lap"). The fibers in the dry lap must be separated from one another prior to introduction to the co-forming process. This may be accomplished by use of a defibrating device such as a shredder or a hammermill, into which the dry lap sheets may be fed and defibrated to separate the individual pulp fibers from the compressed mass of the dry lap, so that the fibers may be, e.g., entrained in a moving airstream for distribution in, e.g., a co-forming process as described herein. The extent of completeness of defibration, or lack thereof, may be controlled by controlling the feed rate of the dry lap into the defibrating device and adjusting the process settings of the defibrating device. In, e.g., a hammermill, such control may be exercised by adjusting the spacing between the hammers and the breaker plate(s) or screen, the rotor speed, and the air flow rate through the hammermill, the latter affecting the time that consolidated masses of pulp fibers remain inside the hammermill and subject to further defibration.

To add texture to the fibrous web structure, the defibration process settings may be adjusted such that the dry lap is incompletely defibrated, and incompletely defribrated consolidated masses of pulp fibers are entrained and passed through the system to the co-forming equipment. It has been found that control over the average size and numerosity of the consolidated masses may be achieved through such adjustment. The inclusion of consolidated masses of pulp fibers in co-forming, and subsequent distribution of the consolidated masses into the core layer of a fibrous web structure, add texture to the structure and provide raised (or thicker) areas and recesses (or thinner areas), perceptible as small "bumps" on the structure, raised in the z-direction, which consumers may find pleasing in that they create tactile pressure points. These raised areas and recesses may also enhance cleaning efficacy of a wet wipe made from the fibrous web structure by providing surface irregularities that tend to capture and sweep soil away from the skin. Thus, the smoothing effect of inclusion of outer scrim layers of meltblown polymer fibers may be countered, while their other benefits may be realized.

Surprisingly, it has been found that such consolidated masses may be included in the fibrous web structure by selection of materials, equipment and adjustment of manufacturing processes by which, when the wet wipe product is wetted with an aqueous liquid composition, the masses are not highly visually discernible (such that they might be perceived by a consumer as defects in the material). It has been found that consolidated masses of wood pulp fibers, of suitably controlled size, substantially reduce in visual discernibility relative to the surrounding areas of the structure when the structured is wetted. In one more particular example, and surprisingly, it has been found that when the consolidated masses comprise mainly hardwood pulp fibers, they are even more likely to have such reduced visual discernibility when the fibrous web structure is wetted. Without intending to be bound by theory it is believed that consolidated masses comprising hardwood fibers may be particularly effective at visibly "disappearing" within the structure when it is wetter, because they are relatively short and fine as compared with softwood pulp fibers. Aspen, birch, or even *Eucalyptus* pulp fibers may be particularly desirable, as they are quite short and fine, and consolidated masses of such fibers are believed to have good ability to substantially visually blend in within the fibrous web structure when it is wetted with an aqueous liquid composition.

Without intending to be bound by theory, it is believed, also, that material comprising recycled fibrous web structure as described herein may serve as a suitable source material for providing consolidated masses as described herein. Such material may be created as longitudinal edges of a fibrous web structure are trimmed off during the manufacture of a web thereof; as non-conforming material is created during line start-up, shut-down, repair, adjustment or maintenance, or alternatively, when scrap material is collected as a result of cutting out of features or components, from rejection of defective articles in which the fibrous web structure may be a component, etc. Such recycled material may be suitably divided into small pieces by, e.g., a shredder, which pieces may themselves be suitable for inclusion as consolidated masses for purposes herein. It is believed that, depending upon their contents, small pieces of such recycled material may serve the above-referenced purpose of visibly blending with the surrounding structure when wetted. Utilizing such material in this manner may also provide an efficient means of recycling the material, which much otherwise be recycled or disposed of by other methods.

For purposes herein, particularly when the source of consolidated masses is cellulose pulp provided as dry lap, a hammermill may be preferred as the defribration device. This is due to the fact that, in a suitably adjusted process, a hammermill produces consolidated masses of fibers with irregular and/or poorly defined edges, as compared with other defibrating devices with cutting blades (such as a shredder) that will produce consolidated masses with more sharply-defined and/or straight edges that may, undesirably, be more visually noticeable in the fibrous web structure. Similarly, any other defibration device that may be adjusted to provide consolidated masses, the majority of which have only irregular and/or poorly defined edges, rather than straight edges, may be deemed suitable.

Figure 15A:
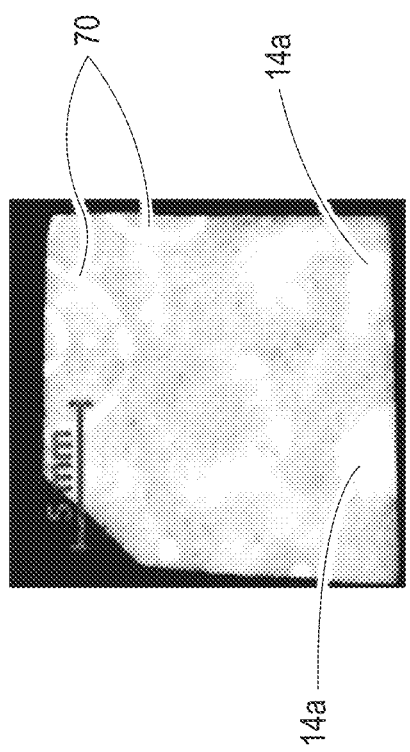
FIG. 15A is a scanning electron microscope image of a plan view of an example of a fibrous web structure having consolidated masses of pulp fibers in a core layer.
Figure 15B:
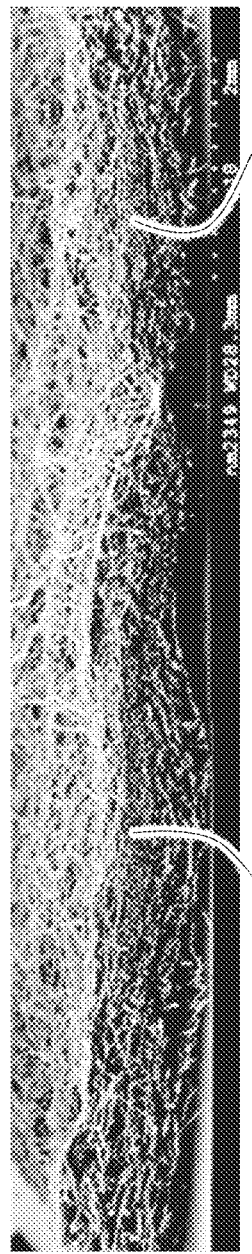
FIG. 15B is a scanning electron microscope image of an end view/section view of the fibrous web structure of shown in FIG. 15A.

FIG. 15A is a scanning electron microscope image of a plan view of an example of a fibrous web structure having consolidated masses 14a of pulp fibers in a core layer. The same masses 14a may be seen in cross-section in FIG. 15B. It can be seen in FIG. 15B that the consolidated masses of pulp fibers 14a help add z-direction texture to the surfaces of the structure.

Use of hardwood pulp fibers and desirably those species identified herein to provide consolidated masses, blended with softwood pulp fibers, may also have the unpredicted benefit of being more controllable with respect to size and numerosity of consolidated masses passed through to the co-forming process. Without intending to be bound by theory, it is believed that the smaller size of hardwood pulp fibers, more desirably any of those species identified herein, provide for greater ease of control and consistency of consolidated mass size in the defibrating process, due in part to relatively small, fine fiber size. This feature allows use of the same hammermill, configured to simultaneously more completely defibrate dry lap of longer softwood pulp fibers, and less completely defibrate dry lap of shorter hardwood pulp fibers. Both softwood pulp and hardwood pulp, dry lap sheets may be fed in parallel to a single hammermill, the hammermill rotor speed, hammer-breaker plate spacing, and airflow rates being adjusted to more completely defibrate the softwood pulp dry lap while producing consolidated masses of incompletely-defibrated hardwood pulp fibers. As noted, the feed rate and process settings may be adjusted and control over the size and numerosity of the consolidated masses of hardwood pulp fibers is readily achievable.

For a good balance of low wet visibility, ease of controlled distributability, and enhancement of surface texture and cleaning efficacy, the consolidated masses are desirably included to a size and extent such that the Density Uniformity Index of the fibrous web structure is from 3.00 to 6.00, and/or the Wet Versus Dry Uniformity Index is from 1.50 to 4.50 when the fibrous web structure is tested using the Density Uniformity Index Method and the Wet Versus Dry Uniformity Index Method, both of which are set forth below. It has been found that these methods enable characterization of the extent of inclusion of consolidated masses of pulp fibers in the fibrous web structure in a way that identifies the beneficial and preferred levels thereof.

The fibrous web structure and/or any product comprising such fibrous web structure may be subjected to any post-processing operations such as embossing operations, printing operations, tuft-generating operations, thermal bonding operations, ultrasonic bonding operations, perforating operations, surface treatment operations such as application of lotions, silicones and/or other materials, folding, and mixtures thereof.

Non-limiting examples of suitable polypropylenes for making the filaments are commercially available from Lyondell-Basell and Exxon-Mobil.

Any hydrophobic or non-hydrophilic materials within the fibrous web structure, such as polypropylene filaments, may be surface treated and/or melt treated with a hydrophilic modifier. Non-limiting examples of surface treating hydrophilic modifiers include surfactants, such as Triton X-100. Non-limiting examples of melt treating hydrophilic modifiers that are added to the melt, such as the polypropylene melt, prior to spinning filaments, include hydrophilic modifying melt additives such as VW351 and/or S-1416 commercially available from Polyvel, Inc. and Irgasurf commercially available from Ciba. The hydrophilic modifier may be associated with the hydrophobic or non-hydrophilic material at any suitable level known in the art. In one example, the hydrophilic modifier is associated with the hydrophobic or non-hydrophilic material at a level of less than about 20% and/or less than about 15% and/or less than about 10% and/or less than about 5% and/or less than about 3% to about 0% by dry weight of the hydrophobic or non-hydrophilic material.

The fibrous web structure may include optional additives, each, when present, at individual levels of from about 0% and/or from about 0.01% and/or from about 0.1% and/or from about 1% and/or from about 2% to about 95% and/or to about 80% and/or to about 50% and/or to about 30% and/or to about 20% by dry weight of the fibrous web structure. Non-limiting examples of optional additives include permanent wet strength agents, temporary wet strength agents, dry strength agents such as carboxymethylcellulose and/or starch, softening agents, lint reducing agents, opacity increasing agents, wetting agents, odor absorbing agents, perfumes, temperature indicating agents, color agents, dyes, osmotic materials, microbial growth detection agents, antibacterial agents and mixtures thereof.

In addition to wipes, the fibrous web structure described herein may be converted to a sanitary tissue product or household cleaning product such as bath tissue or paper towels. It may be convolutedly wound about a core to form a roll. It may be combined with one or more other fibrous web structures as a layer to form a multi-layer product. In one example, a co-formed fibrous web structure may be convolutedly wound about a core to form a roll of co-formed product. A roll product may also be coreless.

Wipe

The fibrous web structure, as described above, may be utilized to form a wipe. "Wipe" is a general term to describe a sheet of material, typically cut from a non-woven web material, adapted for cleaning hard surfaces, food, inanimate objects, toys and body parts. In particular, many currently available wipes (including baby wipes) are adapted for use in cleaning of the perianal area of the body after defecation. Other wipes may be available for cleaning the face or other body parts. Multiple wipes may be attached together by any suitable method to form a mitt.

The material from which a wipe is made should be strong enough to resist tearing during normal use, yet still provide softness to the user's skin, such as a child's tender skin. Additionally, the material should be at least capable of retaining its form for the duration of the user's cleansing experience.

Wipes may be generally of sufficient dimension to allow for convenient handling. Typically, the wipe may be cut and/or folded to such dimensions as part of the manufacturing process. In some instances, the wipe may be cut into individual sheets so as to provide separate wipes which are often stacked, folded and interleaved in consumer packaging. In other embodiments, the wipes may be in a web form where the web has been slit and folded to a predetermined width and provided with means (e.g., perforations) to allow individual wipes to be separated from the web by a user. Wipes sheets divided by perforations may be gathered on a roll (in the manner of conventional dry bathroom tissue or paper towels).

Suitably, an individual wipe may have a length between about 100 mm and about 250 mm and a width between about 140 mm and about 250 mm. In one embodiment, the wipe may be about 200 mm long and about 180 mm wide and/or about 180 mm long and about 180 mm wide and/or about 170 mm long and about 180 mm wide and/or about 160 mm long and about 175 mm wide. The material of the wipe may generally be soft and flexible, potentially having a structured surface to enhance its cleaning performance.

In one example the surface of the fibrous web structure may be substantially, macroscopically flat. In another example the surface of the fibrous web structure may optionally contain raised and/or lowered portions. These can be in the form of logos, indicia, trademarks, geometric patterns, images of the surfaces that the substrate made from the structure is intended to clean (i.e., infant's body, face, etc.). They may be randomly arranged on the surface of the fibrous web structure or be in a repetitive pattern of some form.

In another example the fibrous web structure may be biodegradable. For example the fibrous web structure may be made from a biodegradable material such as a polyesteramide, or high wet strength cellulose.

In one example, the fibrous web structure is used to form a pre-moistened wipe, such as a baby wipe. A plurality of the pre-moistened wipes may be stacked one on top of the other and may be contained in a container, such as a plastic tub or a film wrapper. In one example, the stack of pre-moistened wipes (typically about 40 to 80 wipes/stack) may exhibit a height of from about 50 to about 300 mm and/or from about 75 to about 125 mm. The pre-moistened wipes may comprise a liquid composition, such as a lotion. The pre-moistened wipes may be stored long term in a stack in a liquid impervious container or film pouch without all of the lotion draining from the top of the stack to the bottom of the stack.

In one example, the pre-moistened wipes are present in a stack of pre-moistened wipes that exhibits a height of from about 50 to about 300 mm and/or from about 75 to about 200 mm and/or from about 75 to about 125 mm.

Wipes of the present invention may be saturation loaded with a liquid composition to form a pre-moistened wipe. The loading may occur individually, or after the fibrous web structures or wipes are place in a stack, such as within a liquid impervious container or packet. In one example, the pre-moistened wipes may be saturation loaded with from about 1.5 g to about 6.0 g and/or from about 2.5 g to about 4.0 g of liquid composition per gram of fibrous nonwoven structure.

In one example, the liquid composition comprises water or another liquid solvent. Generally the liquid composition is of sufficiently low viscosity to impregnate the entire structure of the fibrous web structure. In another example, the liquid composition may be primarily present at the fibrous web structure surface and to a lesser extent in the inner structure of the fibrous web structure. In a further example, the liquid composition is releasably carried by the fibrous web structure, that is the liquid composition is carried on or in the fibrous web structure and is readily releasable from the fibrous web structure by applying some force to the fibrous web structure, for example by wiping a surface with the fibrous web structure.

Liquid compositions useful in the present invention may be, but are not necessarily limited to, oil-in-water emulsions. In one example, the liquid composition may be at least 80% and/or at least 85% and/or at least 90% and/or at least 95% by weight water.

When present on or in the fibrous web structure, the liquid composition may be present at a level of from about 10% to about 1000% of the basis weight of the fibrous web structure and/or from about 100% to about 700% of the basis weight of the fibrous web structure and/or from about 200% to about 500% and/or from about 200% to about 400% of the basis weight of the fibrous web structure.

The liquid composition may comprise an acid. Non-limiting examples of acids that may be included in the liquid composition are adipic acid, tartaric acid, citric acid, maleic acid, malic acid, succinic acid, glycolic acid, glutaric acid, malonic acid, salicylic acid, gluconic acid, polymeric acids, phosphoric acid, carbonic acid, fumaric acid and phthalic acid and mixtures thereof. Suitable polymeric acids can include homopolymers, copolymers and terpolymers, and may contain at least 30 mole % carboxylic acid groups. Specific examples of suitable polymeric acids useful herein include straight-chain poly(acrylic) acid and its copolymers, both ionic and nonionic, (e.g., maleic-acrylic, sulfonic-acrylic, and styrene-acrylic copolymers), those cross-linked polyacrylic acids having a molecular weight of less than about 250,000, preferably less than about 100,000 poly (α-hydroxy) acids, poly (methacrylic) acid, and naturally occurring polymeric acids such as carageenic acid, carboxy methyl cellulose, and alginic acid. In one example, the liquid composition comprises citric acid and/or citric acid derivatives.

The liquid composition may also contain salts of the acid or acids used to lower the pH, or another weak base to impart buffering properties to the fibrous web structure. The buffering response is due to the equilibrium which is set up between the free acid and its salt. This allows the fibrous web structure to maintain its overall pH despite encountering a relatively high amount of bodily waste as would be found post urination or defecation in a baby or adult. In one embodiment the acid salt would be sodium citrate. The amount of sodium citrate present in the lotion would be between 0.01 and 2.0%, alternatively 0.1 and 1.25%, or alternatively 0.2 and 0.7% of the lotion.

In one example, the liquid composition does not contain any preservative compounds.

In addition to the above ingredients, the liquid composition may comprise additional ingredients. Non-limiting examples of additional ingredients that may be included in the liquid composition include: skin conditioning agents (emollients, humectants) including waxes such as petrolatum, cholesterol and cholesterol derivatives; di- and triglycerides including sunflower oil and sesame oil; silicone oils such as dimethicone copolyol, caprylyl glycol; and acetoglycerides such as lanolin and its derivatives; emulsifiers; stabilizers; surfactants including anionic, amphoteric, cationic and nonionic surfactants; colorants; chelating agents including EDTA; sun screen agents; solubilizing agents; perfumes; opacifying agents; vitamins; viscosity modifiers such as xanthan gum; astringents; and external analgesics.

The liquid composition also may be formulated as described in any of, for example, U.S. Pat. Nos. 8,221,774 and 8,899,003; and U.S. patent application Ser. Nos. 11/717, 928; 11/807,139; 12/105,654; 12/611,310; 12/771,391; 12/976,180; 13/220,982; 13/752,639; 14/330,171; 14/493, 469; 14/602,692; and 62/057,297. An opacifying lotion formulation such as described in, for example, U.S. patent application Ser. No. 13/220,982, may be particularly useful for imparting opacity to, or enhancing opacity of, a fibrous web structure, particularly one with a lower basis weight, e.g., from 40-80 gsm, 40-70 gsm, or even 40-60 gsm, having the effect of interacting with the pulp fibers (including the relatively fine hardwood pulp fibers, when included) in a synergistic way to increase opacity of the structure and thereby enhance an appearance of robustness and barrier functionality of a wet wipe made from the fibrous nonwoven structure.

Wipes of the present invention may be placed in the interior of a container, which may be liquid impervious, such as a plastic tub or a sealable packet, for storage and eventual sale to the consumer. The wipes may be folded and stacked. The wipes of the present invention may be folded in any of various known folding patterns, such as C-folding, Z-folding and quarter-folding. Use of a Z-fold pattern may enable a folded stack of wipes to be interleaved with overlapping portions. Alternatively, the wipes may include a continuous strip of material which has perforations between each wipe and which may be arranged in a stack or wound into a roll for dispensing, one after the other, from a container, which may be liquid impervious.

The fibrous web structure or wipes of the present invention may further include prints, which may provide aesthetic appeal. Non-limiting examples of prints include figures, patterns, letters, pictures and combinations thereof.

Method for Making a Co-Formed Fibrous Web Structure

Figure 8:
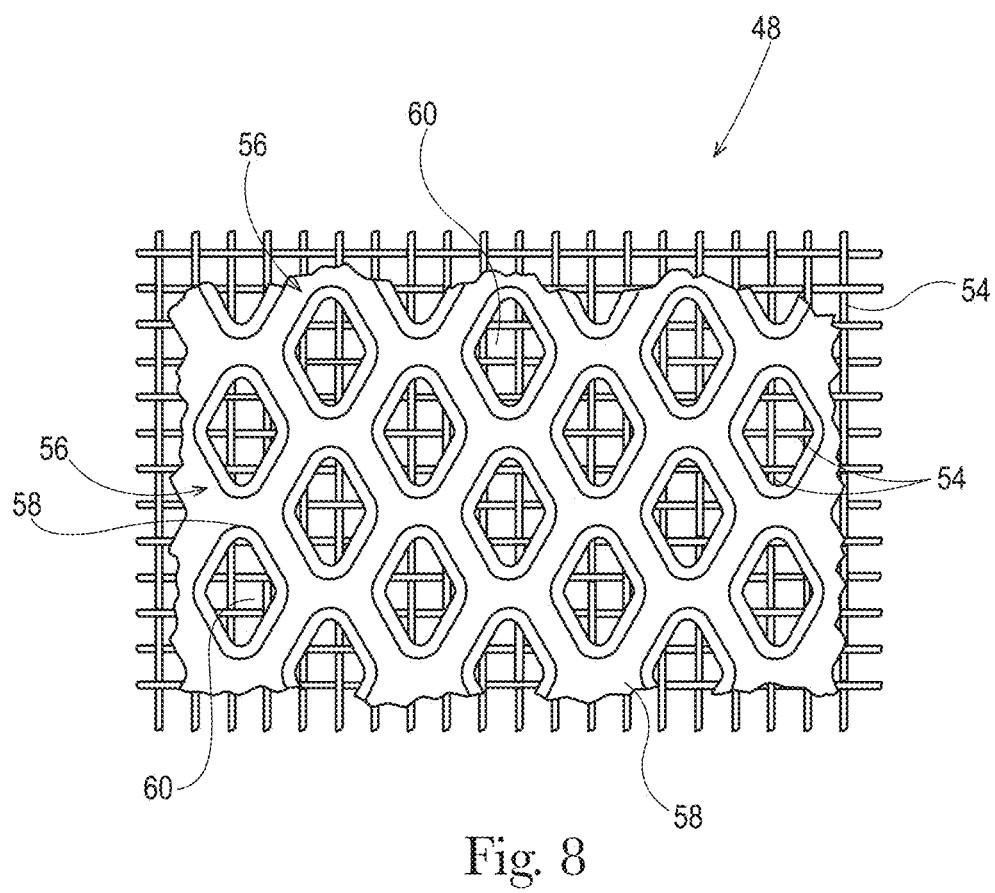
FIG. 8 is a schematic illustration of an example of a patterned belt for use in a process.

A non-limiting example of a method for making a co-formed fibrous web structure or a core layer thereof according to the present invention is schematically illustrated in FIG. 7A. The method illustrated in FIG. 7A comprises the step of mixing a plurality of fibers 14 with a plurality of filaments 12. In one example, the fibers 14 are wood pulp fibers, such as SSK fibers and/or *Eucalyptus* fibers, and the filaments 12 are polypropylene filaments. The fibers 14 may be combined with the filaments 12, such as by being delivered to a stream of filaments 12 from a hammermill 42 via a fiber spreader 44 to form a mixture of filaments 12 and fibers 14. The filaments 12 may be created by meltblowing from a meltblowing spinneret 46. The mixture of fibers 14 and filaments 12 are collected on a collection device, such as a forming belt 48 to form a fibrous web structure 50. The collection device may be a patterned and/or molded belt that results in the fibrous web structure exhibiting a surface pattern, such as a non-random, repeating pattern of micro-regions. The patterned and/or molded belt may have a three-dimensional pattern on it that is imparted to the fibrous web structure 50 during the process. For example, a patterned belt 48, as shown in FIG. 8, may comprise a reinforcing structure, such as a fabric 54, upon which a polymer resin 56 is molded or otherwise applied to reflect a three-dimensional pattern. The pattern may comprise a continuous or semi-continuous network 58 of the polymer resin 56 within which one or more discrete conduits 60 are arranged.

In another example schematically illustrated in FIG. 7B, a multilayer fibrous web structure 50 with outer scrim layers on both sides may be made in a single-pass, direct-forming process. "Single pass" means that the fibrous web structure is formed in a single continuous process, with no intervening gathering or storage of component layers, e.g., on a roll. "Direct forming" means that each component layer of the structure following the first-formed layer is formed directly over the first layer or a later-formed layer, rather than being formed separately.

In a single-pass, direct forming process, a first meltblowing spinneret 46a may be used to spin a plurality of first meltblown filaments 12a that may be accumulated on a moving forming surface, such as the surface of a moving forming belt 48, to form a first scrim layer.

Downstream in the process, a configuration of co-forming equipment that may include co-form meltblowing spinneret 46b, a fiber spreader 44, and a mixing box such as co-form box 74, may be arranged and configured to deliver meltblown filaments and air-entrained pulp fibers, respectively to the mixing box such as co-form box 74. In the co-form box the filaments and fibers may be blended, entangled and entrained in an air stream. Differing first and second dry lap sheets 71, 72 may be fed into a defibrating apparatus 75 at controlled rates. First dry lap sheet may comprise a first cellulose pulp, and second dry lap sheet may comprise a second cellulose pulp, wherein the first and second cellulose pulps comprise hardwood and softwood pulps, or medium-length fiber pulps and short fiber pulps, or vice versa. In one example, the hardwood, or short fiber, pulp, may comprise aspen, birch or *Eucalyptus* fiber pulp. In one example, the softwood, or medium-length fiber, pulp, may comprise SSK fiber pulp. Defibrating apparatus 75 may be a hammermill, or pair or plurality of hammermills, or any other suitable defibrating apparatus or plurality or combination thereof. In one example, defibrating apparatus 75 may include a defibrating apparatus configured to produce, with process variables adjusted to produce, consolidated masses of fibers, the majority of which have irregular or poorly defined edges. A combination of fibers and consolidated masses thereof may be entrained in an airstream and thereby carried from the defibrating apparatus 75 to a fiber spreader 44. A co-form meltblowing spinneret 46b and the fiber spreader 44 may be arranged and configured to deliver meltblown filaments and air-entrained pulp fibers and consolidated masses thereof, respectively, to a mixing box such as co-form box 74, wherein the filaments, fibers and consolidated masses thereof are blended and entangled to form a co-form stream 14a, which may then be directed to a moving forming surface (such as belt 48) to accumulate and form a co-form layer. In the example illustrated in FIG. 7B, the co-form layer may be accumulated and formed directly over and overlying the first scrim layer. In some examples, a plurality of configurations of co-forming equipment may be arranged in succession to deliver a plurality of co-form streams 14a in succession to build up the thickness and basis weight of the co-form layer accumulation. This may enable greater manufacturing line speed than use of only a single configuration of co-forming equipment, and may also provide a mechanism for increasing or regulating basis weight of the co-form layer when the operating speed of belt 48 is governed by other concerns, e.g., the desired basis weight of the scrim layer(s).

Further downstream in the process, a second meltblowing spinneret 46b may be used to spin a plurality of second meltblown filaments 12b that may be accumulated on a moving forming surface, such as the surface of moving forming belt 48, to form a second scrim layer. In the example illustrated in FIG. 7B (schematically illustrating a single-pass, direct forming process), the second scrim layer may be accumulated and formed directly over and overlying the previously-formed co-form layer.

The fiber spreader(s) 44 may be configured, and may comprise equipment including an educator, as described in, for example, U.S. Patent App. Ser. No. 62/094,087. The co-form box may be configured as described in, for example, U.S. Patent App. Ser. No. 62/094,089.

As reflected in FIGS. 7A and 7B, the process for forming the fibrous web structure may be a direct forming process in which the layers of the structure are formed sequentially by depositing components of overlying layers directly onto previously deposited components of underlying layers—as contrasted with a process in which one or more of the scrim and/or co-form layers are formed separately and, e.g., conveyed as a fully-formed layer to the fibrous web structure forming process. A direct forming process may be preferred for purposes herein in which comparatively low basis weight scrim layers formed of meltblown filaments are contemplated, as such layers may in ordinary circumstances be too weak (i.e., have insufficient machine-direction tensile strength) to be self-supporting and rolled/unrolled, or otherwise conveyed, separately. In addition, it is believed that a direct forming process provides another benefit. Without intending to be bound by theory, it is believed that formation of a layer by depositing fibers and/or filaments directly onto and over another previously-formed layer results in comparatively greater intermingling and/or entangling of fibers and/or filaments at the interface between the layers, providing a more unitized multilayer fibrous web structure in which the layers are less likely to separate, e.g., in downstream processes or in consumer use of an end product made from the fibrous web structure. A single-pass, direct forming process may be more efficient by enabling greater manufacturing speeds, and less use of plant space and resources.

Figure 9A:
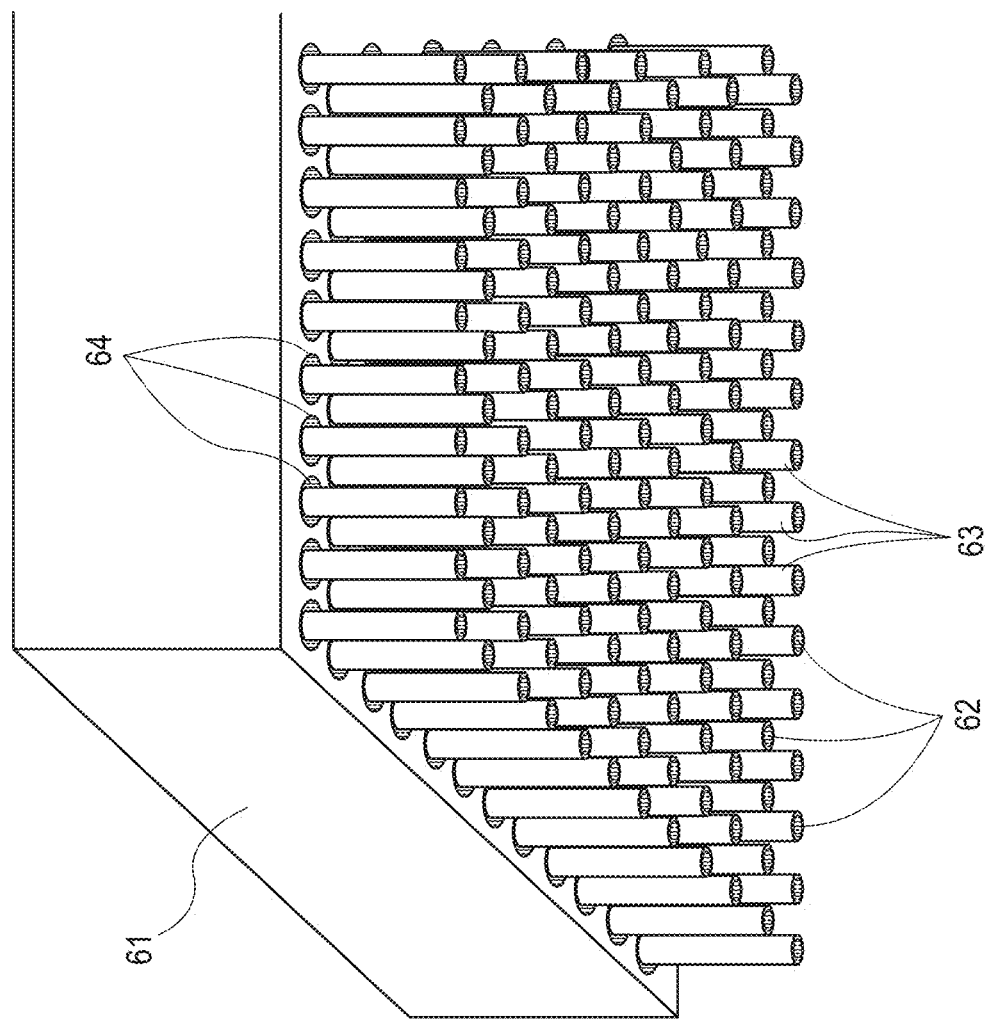
FIG. 9A is a schematic perspective-view illustration of a portion of an example of a spinneret with a plurality of nozzles and attenuation fluid outlets.
Figure 9B:
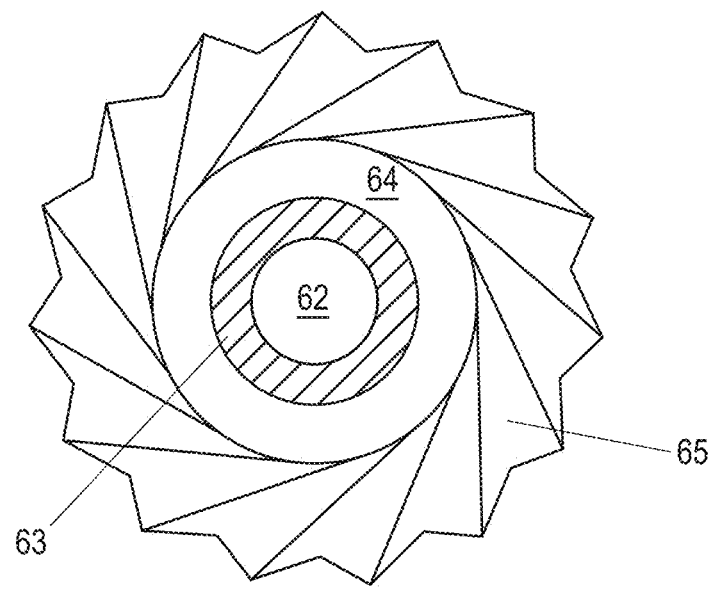
FIG. 9B is a schematic end-view illustration of an example of a nozzle in a spinneret with a melt exit hole and an attenuation fluid outlet useful in spinning filaments.

Referring to FIGS. 9A and 9B, the filament components of the fibrous web structure may be made using a meltblowing spinneret 46 comprising a plurality of filament nozzles 63 that may be arranged in rows, from which filaments are spun. Melted polymer may be extruded under pressure through the nozzles 63, whereby it is forced through the nozzles to exit as polymer streams from melt outlets 62. The spinneret may include annular attenuating fluid (e.g., air) outlets 64 about the nozzles, from which heated, pressurized gaseous fluid (e.g. air) may be caused to exit the spinnerets at high speed and flow along the lengths of the nozzles and past their ends, as the polymer streams exit the melt outlets 62. The nozzles or spinneret may include features to affect direction and/or features of the fluid streams (such as to induce or increase turbulence) about the exiting melted polymer streams, such as flutes 65. The hot gaseous fluid (e.g., air) flowing at high speed past the ends of the nozzles will entrain the polymer streams and thereby lengthen and attenuate them, to create fine filaments.

As shown in FIGS. 9A and 9B, in some examples, the nozzle may be positioned within an attenuating fluid outlet. The melt outlet 62 may be concentrically or substantially concentrically positioned within the attenuating fluid outlet 64 such as is suggested in FIGS. 9A and 9B.

Following attenuation, the filaments may be air quenched with cooling air. The filaments forming the scrim layers (e.g., those from spinnerets 46a and 46c, as shown in the example of FIG. 7B) may be air-quenched, or mist quenched with a mixture of cooling air and water droplets. Mist-quenching is an efficient way to increase the rate of cooling of the scrim filaments and impart comparatively greater tensile strength and elongation capability to them. The water droplets evaporate quickly, removing heat, when they contact the combination of hot air and hot polymer streams, such that a subsequent drying step is not necessary. Chilling the cooling air (e.g. via passing it over a heat exchanger through which coolant fluid circulates, such as an evaporator) is an alternative method of achieving more rapid cooling of the filaments, but is less effective and energy-efficient than mist-quenching. However, mist-quenching may in some circumstances not be deemed suitable for the filaments from the co-form meltblowing spinneret, as this may cause water to be introduced into the co-forming process, causing complications that may include clumping of pulp fibers, or the necessity, complication and expense of an additional drying step.

Following quenching the filaments may be directed directly at a moving collecting and/or forming surface such as a forming belt 48 (e.g., as shown in FIGS. 7A, 7B) to form scrim layer(s), or alternatively, may be directed into a co-form box 47 (e.g., as shown in FIG. 7B) to form a co-form layer.

Figure 10:
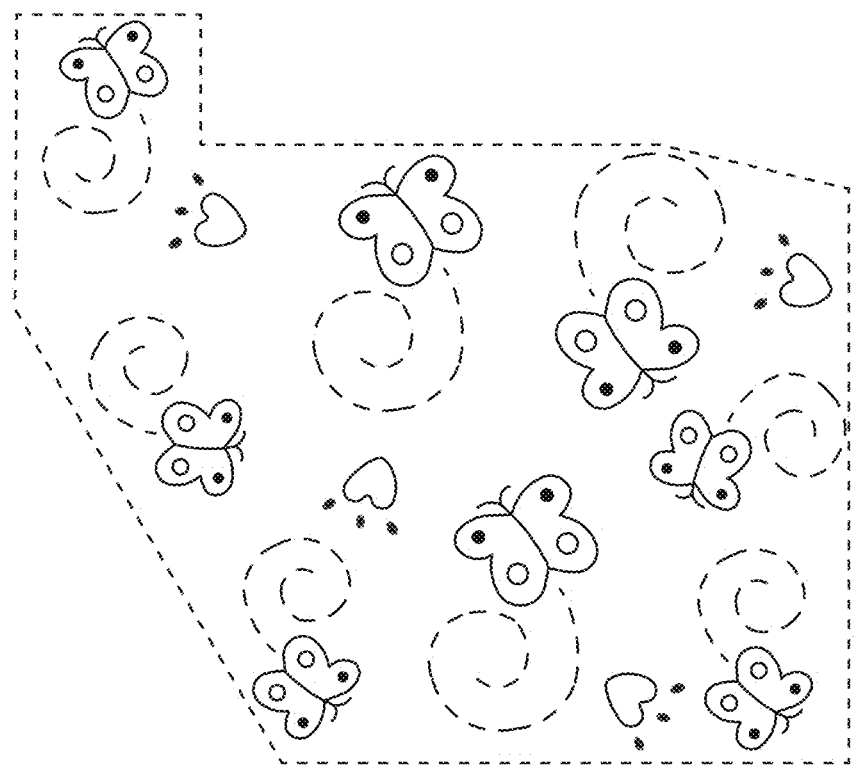
FIG. 10 is an example of a thermal bond pattern that can be imparted to a fibrous web structure.
Figure 11:
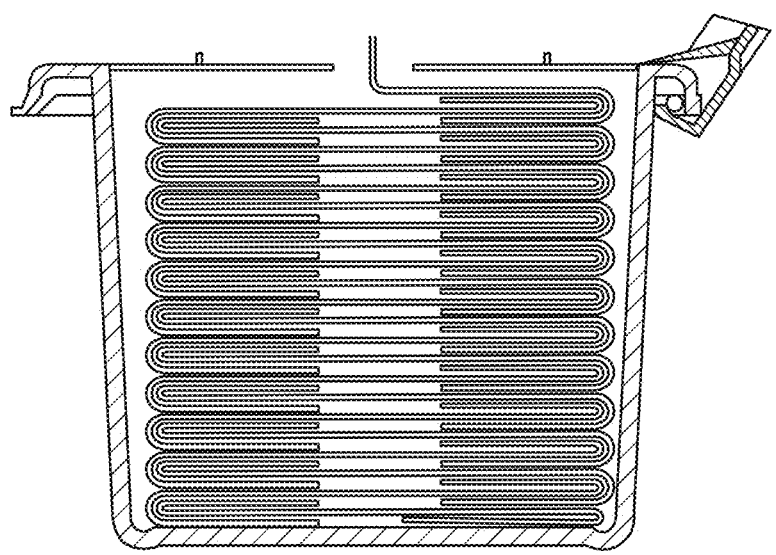
FIG. 11 is a schematic illustration of an example of a stack of wet wipes in a tub.

After the layers have been formed or deposited on the collecting surface, such as a belt 48, they may be calendered, for example, while the deposited layers of filaments and fibers are still on the collection device, or downstream thereof. In one example as shown in FIG. 7B, the accumulated first scrim layer, co-form layer, and second scrim layer may be passed together into the nip 49c between a pair of calender rollers 49a, 49b. One or both of the calender rollers may have etched, machined or otherwise formed on its cylindrical surface a pattern of bonding protrusions having functional and/or decorative features and appearance; one possible example (among a practically unlimited number of variants) is shown in FIG. 10. One or both calender rollers 49a, 49b may be heated, or a source of heat energy (such as, for example, ultrasound energy) may be supplied at the nip, and the rollers may be configured to exert a controlled amount of pressure on the layers in the nip. Thus, as the accumulated first scrim layer, co-form layer, and second scrim layer pass through the nip, the fibers and filaments thereof are consolidated in the z-direction and the polymer filaments are heated and compressed together beneath the bonding protrusions of the roller bearing the same, and may be at least partially fused to form thermal bonds, extending through the structure in the z-direction and bonding the respective scrim layers 38, 40 to the structure at bonds 70, as may be appreciated from FIG. 6C. In order to most effectively form such thermal bonds, it may be desired that the polymer(s) or blend(s) thereof forming the filaments of the respective scrim layers 38, 40 and the filaments in the co-form layer(s) 36 be of like chemistry. As reflected in FIG. 7B, formation of the first scrim layer, core layer(s) and second scrim layer, and consolidation and thermal bonding of the layers to form a bonded fibrous web structure, may be performed in a single pass, direct forming process, i.e., with no intervening conveying, gathering or storing of layers occurring between the formation thereof, and formation of the completed fibrous web structure. This may be process- and cost-efficient, and also removes the need for a minimum basis weight for scrim layers sufficient to make them self-supporting for purposes of conveying separately and/or gathering on a roll. In turn, this enables inclusion of relatively low basis weight scrim layers as contemplated herein, in the fibrous web structure.

The surface area occupied by the bonds 70 relative to the total surface area of the fibrous web structure may be expressed as bond area percentage, and is calculated as the total surface area occupied by the bonds 70, divided by the overall surface area of a side of the fibrous web structure 50 on which the bonds appear, ×100%. Bond area percentage on a fibrous web structure approximately reflects bonding area percentage of the raised (bonding) surfaces of the bonding protrusions on a calender bonding roller, divided by the total surface area of the circumscribing cylindrical shape of the portion of the calender bonding roller that contacts the web structure in the nip. Bond area percentage may be increased or decreased by altering the design of the pattern of bonding protrusions on the calendar bonding roller. Bonding protrusions having larger bonding surface area and/or more dense spacing impart comparatively greater bond area percentage to the web structure, while bonding protrusions having smaller bonding surface area and/or less dense spacing impart comparatively lesser bond area percentage to the web structure. Generally, it is believed that, within the practical operating ranges contemplated herein, greater bond area percentage may impart comparatively greater machine and cross direction tensile strength, but also comparatively greater stiffness, in the web structure. Conversely, comparatively lesser bond area percentage may impart comparatively less machine and cross direction tensile strength, and comparatively less stiffness (i.e., greater flexibility), in the web structure. For purposes of the present disclosure and of striking the best balance between strength and consumer preferences in the fibrous web structure, it may be desired that thermal bond area percentage be in a range of from 2% to 12%, more preferably from 3% to 10%, even more preferably from 4% to 8%, and still more preferably from 5% to 7%.

In addition, the fibrous web structure 50 may be subjected to other post-processing operations such as embossing, tuft-generating operations, moisture-imparting operations, and surface treating operations to form the finished fibrous web structure. One example of a surface treating operation that the fibrous web structure may be subjected to is the surface application of an elastomeric binder, such as ethylene vinyl acetate (EVA), latexes, and other elastomeric binders. Such an elastomeric binder may aid in reducing the lint created from the fibrous web structure during use by consumers. The elastomeric binder may be applied to one or more surfaces of the fibrous web structure in a pattern, especially a non-random, repeating pattern of microregions, or in a manner that covers or substantially covers the entire surface(s) of the fibrous web structure.

In one example, the fibrous web structure 50 and/or the finished fibrous web structure may be combined with one or more other fibrous web structures. For example, another fibrous web structure, such as a filament-containing fibrous web structure, such as a polypropylene filament fibrous web structure may be associated with a surface of the fibrous web structure 50 and/or the finished fibrous web structure. The polypropylene filament fibrous web structure may be formed by meltblowing polypropylene filaments (filaments that comprise a second polymer that may be the same or different from the polymer of the filaments in the fibrous web structure 50) onto a surface of the fibrous web structure 50 and/or finished fibrous web structure. In another example, the polypropylene filament fibrous web structure may be formed by meltblowing filaments comprising a second polymer that may be the same or different from the polymer of the filaments in the fibrous web structure 50 onto a collection device to form the polypropylene filament fibrous web structure. The polypropylene filament fibrous web structure may then be combined with the fibrous web structure 50 or the finished fibrous web structure to make a two-layer fibrous web structure—three-layer if the fibrous web structure 50 or the finished fibrous web structure is positioned between two layers of the polypropylene filament fibrous web structure like that shown in FIG. 4 for example. The polypropylene filament fibrous web structure may be thermally bonded to the fibrous web structure 50 or the finished fibrous web structure via a thermal bonding operation.

In yet another example, the fibrous web structure 50 and/or finished fibrous web structure may be combined with a filament-containing fibrous web structure such that the filament-containing fibrous web structure, such as a polysaccharide filament fibrous web structure, such as a starch filament fibrous web structure, is positioned between two fibrous web structures 50 or two finished fibrous web structures like that shown in FIG. 6A for example.

In one example, the method for making a fibrous web structure comprises the step of combining a plurality of filaments and optionally, a plurality of fibers to form a fibrous web structure that exhibits the properties of the fibrous web structures described herein. In one example, the filaments comprise thermoplastic filaments. In one example, the filaments comprise polypropylene filaments. In still another example, the filaments comprise natural polymer filaments. The method may further comprise subjecting the fibrous web structure to one or more processing operations, such as calendaring the fibrous web structure. In yet another example, the method further comprises the step of depositing the filaments onto a patterned belt that creates a non-random, repeating pattern of micro regions.

In still another example, two layers of fibrous web structure 50 comprising a non-random, repeating pattern of microregions may be associated with one another such that protruding microregions, such as pillows, face inward into the two-layer fibrous web structure formed.

The process for making a fibrous web structure 50 may be close coupled (where the fibrous web structure is convolutedly wound into a roll prior to proceeding to a converting operation) or directly coupled (where the fibrous web structure is not convolutedly wound into a roll prior to proceeding to a converting operation) with a converting operation to emboss, print, deform, surface treat, thermal bond, cut, stack or other post-forming operation known to those in the art.

For purposes of the present invention, direct coupling means that the fibrous web structure 50 can proceed directly into a converting operation rather than, for example, being convolutedly wound into a roll and then unwound to proceed through a converting operation.

In one example, the fibrous web structure is embossed, cut into sheets, and collected in stacks of fibrous web structures.

A process according the present disclosure may include preparing individual rolls and/or sheets and/or stacks of sheets of fibrous web structure and/or sanitary tissue product comprising such fibrous web structure(s) that are suitable for consumer use.

Examples Contemplated

The following non-limiting examples are contemplated within the scope of this description:

1. A wet wipe comprising a fibrous web structure wetted with an aqueous liquid composition, the fibrous web structure comprising:

from 10 percent by weight to 40 percent by weight, more preferably from 15 percent by weight to 35 percent by weight, and even more preferably from 20 percent by weight to 30 percent by weight melt spun polymer filaments; and from 60 percent by weight to 90 percent by weight cellulose pulp fibers, more preferably from 65 percent by weight to 85 percent by weight cellulose pulp fibers, and still more preferably from 70 percent by weight to 80 percent by weight cellulose pulp fibers, wherein the fibrous web structure has a Density Uniformity Index of from 3.00 to 6.00.

2. A wet wipe comprising a fibrous web structure wetted with an aqueous liquid composition, the fibrous web structure comprising:

from 10 percent by weight to 40 percent by weight, more preferably from 15 percent by weight to 35 percent by weight, and even more preferably from 20 percent by weight to 30 percent by weight melt spun polymer filaments; and from 60 percent by weight to 90 percent by weight cellulose pulp fibers, more preferably from 65 percent by weight to 85 percent by weight cellulose pulp fibers, and still more preferably from 70 percent by weight to 80 percent by weight cellulose pulp fibers, wherein the fibrous web structure has a Wet Versus Dry Uniformity Index of from 1.50 to 4.50.

3. A wet wipe comprising a fibrous web structure wetted with an aqueous liquid composition, the fibrous web structure comprising:

from 10 percent by weight to 40 percent by weight, more preferably from 15 percent by weight to 35 percent by weight, and even more preferably from 20 percent by weight to 30 percent by weight melt spun polymer filaments; and from 60 percent by weight to 90 percent by weight cellulose pulp fibers, more preferably from 65 percent by weight to 85 percent by weight cellulose pulp fibers, and still more preferably from 70 percent by weight to 80 percent by weight cellulose pulp fibers, wherein the fibrous web structure has a Density Uniformity Index of from 3.00 to 6.00 and a Wet Versus Dry Uniformity Index of from 1.50 to 4.50.

4. A wet wipe comprising a fibrous web structure wetted with an aqueous liquid composition, the fibrous web structure comprising:

from 10 percent by weight to 40 percent by weight, more preferably from 15 percent by weight to 35 percent by weight, and even more preferably from 20 percent by weight to 30 percent by weight meltblown polymer filaments; and from 60 percent by weight to 90 percent by weight cellulose pulp fibers, more preferably from 65 percent by weight to 85 percent by weight cellulose pulp fibers, and still more preferably from 70 percent by weight to 80 percent by weight cellulose pulp fibers, wherein the fibrous web structure has first and second outer scrim layers comprising a first portion of said melt spun polymer filaments, and an inner core layer comprising said cellulose pulp fibers, wherein a portion of the cellulose pulp fibers comprises consolidated masses of the cellulose pulp fibers.

5. The fibrous web structure of example 4 wherein the inner core layer comprises a second portion of said melt spun polymer filaments.

6. A wet wipe comprising a fibrous web structure wetted with an aqueous liquid composition, the fibrous web structure comprising:

from 10 percent by weight to 40 percent by weight, more preferably from 15 percent by weight to 35 percent by weight, and even more preferably from 20 percent by weight to 30 percent by weight meltblown polymer filaments; and from 60 percent by weight to 90 percent by weight cellulose pulp fibers, more preferably from 65 percent by weight to 85 percent by weight cellulose pulp fibers, and still more preferably from 70 percent by weight to 80 percent by weight cellulose pulp fibers, wherein a portion of the cellulose pulp fibers comprises consolidated masses of cellulose pulp fibers selected from the group consisting of short pulp fibers, hardwood pulp fibers, aspen pulp fibers, birch pulp fibers, *Eucalyptus* pulp fibers and combinations thereof.

7. A fibrous web structure fibrous web structure comprising:

from 10 percent by weight to 40 percent by weight, more preferably from 15 percent by weight to 35 percent by weight, and even more preferably from 20 percent by weight to 30 percent by weight meltblown polymer filaments;

from 60 percent by weight to 90 percent by weight cellulose pulp fibers, more preferably from 65 percent by weight to 85 percent by weight cellulose pulp fibers, and still more preferably from 70 percent by weight to 80 percent by weight cellulose pulp fibers; and consolidated masses of the cellulose pulp fibers; and wherein the consolidated masses are visually discernible when the fibrous web structure has a water content of less than about 10% of the dry weight of the structure, and are of comparatively reduced visual discernibility when the fibrous web structure has a water content of 200% or more of the dry weight of the structure.

8. The wet wipe of any of examples 1-3 wherein a portion of the cellulose pulp fibers comprises consolidated masses of the cellulose pulp fibers.

9. The wet wipe of any of examples 4-6 or 8, wherein the consolidated masses are visually discernible when the fibrous web structure has a water content of less than about 10% of the dry weight of the structure, and are of comparatively reduced visual discernibility when the fibrous web structure has a water content of 200% or more of the dry weight of the structure.

10. The fibrous web structure or wet wipe of either of examples 7 or 9, wherein the consolidated masses are not visually discernible when the fibrous web structure has a water content of about 500% or more of the dry weight of the structure.

11. The fibrous web structure or wet wipe of example 10 wherein the consolidated masses are not visually discernible when the fibrous web structure has a water content of about 400% or more of the dry weight of the structure.

12. The fibrous web structure or wet wipe of example 11 wherein the consolidated masses are not visually discernible when the fibrous web structure has a water content of about 300% or more of the dry weight of the structure.

13. The fibrous web structure or wet wipe of example 12 wherein the consolidated masses are not visually discernible when the fibrous web structure has a water content of about 200% or more of the dry weight of the structure.

14. The fibrous web structure or wet wipe of any of examples 4-13 wherein the consolidated masses comprise fibers selected from the group consisting of short fibers, hardwood fibers, aspen fibers, birch fibers, *Eucalyptus* fibers, and combinations thereof.

15. The fibrous web structure or wet wipe of any of examples 1-3 or 6-14 further comprising first and second outer scrim layers comprising a first portion of said melt spun polymer filaments, and an inner core layer comprising said cellulose pulp fibers.

16. The fibrous web structure or wet wipe of examples 4 or 15 wherein each of the first and second outer scrim layers has a basis weight equal to or greater than 0.1 gsm.

17. The fibrous web structure or wet wipe of any of examples 4, 15 or 16 wherein scrim layers have a combined basis weight of 0.2 gsm to 6 gsm, more preferably a basis weight of 0.6 gsm to 5 gsm.

18. The fibrous web structure or wet wipe of any of examples 14-17 wherein the inner core layer comprises a second portion of said melt spun polymer filaments.

19. The fibrous web structure or wet wipe of any of examples 15-18 wherein the first portion of melt spun polymer filaments comprises meltblown filaments.

20. The fibrous web structure of wet wipe of example 19 wherein both first and second outer scrim layers comprise meltblown filaments.

21. The fibrous web structure or wet wipe of any of examples 15-20 wherein the inner core layer comprises a second portion of said melt spun polymer filaments.

22. The fibrous web structure of wet wipe of example 21 wherein the second portion of said melt spun polymer filaments comprises melt blown filaments.

23. The fibrous web structure or wet wipe of any of examples 19 or 20 wherein the meltblown filaments have been mist-quenched following spinning.

24. The wet wipe or fibrous web structure of any of the preceding examples wherein the cellulose pulp fibers comprise fibers selected from the group consisting of long fibers, medium length fibers, softwood pulp fibers, SSK pulp fibers and combinations thereof.

25. The wet wipe or fibrous web structure of any of the preceding examples wherein the cellulose pulp fibers comprise a blend of: fibers selected from the group consisting of short fibers, hardwood fibers, aspen fibers, birch fibers, *Eucalyptus* fibers, and combinations thereof; and fibers selected from the group consisting of long fibers, medium length fibers, softwood pulp fibers, SSK pulp fibers and combinations thereof.

26. The fibrous web structure or wet wipe of any of the preceding examples wherein the cellulose pulp fibers comprise a blend of hardwood and softwood pulp fibers in a ratio of 60:40 to 90:10, more preferably 65:35 to 85:15, and still more preferably 70:30 to 80:20, weight of softwood pulp fibers to weight of hardwood pulp fibers present in the fibrous nonwoven structure.

27. The fibrous web structure or wet wipe of any of examples 4, 5 or 15-23 wherein the first and second outer scrim layers comprise filaments formed of polymer(s) or blend(s) thereof of like chemistry.

28. The fibrous web structure or wet wipe of example 27 wherein the polymer(s) or blend(s) thereof comprise polyolefin, preferably polypropylene.

29. The fibrous web structure or wet wipe of any of the preceding examples wherein the fibrous web structure bears an impressed pattern of thermal bonds at which polymer filaments of each of the first and second outer scrim layers are deformed and fused.

30. The fibrous web structure or wet wipe of any of examples 4-14 or any examples dependent thereon, wherein the majority of the consolidated masses lack any straight edges.

31. The fibrous web structure or wet wipe of any of examples 4-14 or any examples dependent thereon wherein the consolidated masses have been produced in a hammermill.

32. The fibrous web structure or wet wipe of any of the preceding examples wherein the fibrous web structure has a basis weight of from 40 gsm to 90 gsm.

Non-Limiting Example of Process for Making a Fibrous Web Structure of the Present Invention The following example was manufactured on a pilot line in a two-pass, direct forming process as follows:

Co-Formed Core Layer

A 21%:27.5%47.5%:4% blend, respectively, of PH835 polypropylene (LyondellBasell, London, UK): Metocene MF650W polypropylene (LyondellBasell, London, UK): Metocene MF650X (LyondellBasell, London, UK): White 412951 (Ampacet Corporation, Tarrytown, N.Y.) whitening agent/opacifier is dry blended, to form a melt blend. The melt blend is heated to about 400° F.-405° F. through a melt extruder. A 15.5 inch wide Biax 12 row spinnerette with 192 nozzles per cross-direction inch, commercially available from Biax Fiberfilm Corporation, is utilized. 40 nozzles per cross-direction inch of the 192 nozzles have a 0.018 inch inside diameter melt outlet hole while the remaining nozzles are plugged, i.e., there is no opening in the nozzle. Approximately 0.18 grams per (open) hole per minute (ghm) of the melt blend is extruded from the open nozzles to form meltblown filaments from the melt blend. Approximately 415 SCFM of compressed air is heated such that the air has a temperature of about 395° F. at the spinnerette. Approximately 295 g/minute of Golden Isle 4825 semi-treated SSK pulp (Georgia-Pacific, Atlanta, Ga.) is defibrated through a hammermill to form SSK wood pulp fibers. Simultaneously and in the same hammermill, approximately 125 g/minute of *Eucalyptus* Hardwood Kraft (EHK) pulp (Fibria Cellulose S.A., Sao Paulo, Brazil) is partially defibrated to form EHK wood pulp consolidated masses.

Approximately 2100 SCFM Air at a temperature of about 80° F. and about 75% relative humidity (RH) is drawn into the hammermill.

The pulp fibers and consolidated masses are conveyed as described in U.S. Pat. App. No. 62/170,176 using a motive air mass flow of approximately 1200 SCFM via two fiber spreaders. The fiber spreaders turn the pulp fibers and consolidated masses and distribute them in the cross direction such that they are injected into the stream of meltblown filaments at a 45° angle through two 4 inch×15 inch cross-direction (CD) slots. The pulp conveying ductwork and geometry are as described in U.S. Pat. App. Ser. No. 62/170,169 (and 62/170,172). A forming box surrounds the area where the meltblown filaments and pulp fibers and consolidated masses are commingled. This forming box is designed to reduce the amount of air allowed to enter or escape from this commingling area. The forming box is as described in U.S. Pat. App. Ser. No. 62/170,179. A forming vacuum pulls air through a moving collection surface, such as a non-patterned forming belt or through-air-drying fabric, thus collecting and accumulating the commingled meltblown filaments, pulp fibers and consolidated masses to form a fibrous structure batt. An example of such a fabric is Albany International Electrotech F541-28I. The forming vacuum level is adjusted to prevent excessive air from escaping from the forming box. The fibrous structure batt formed by this process comprises about 77% by dry fibrous structure weight of pulp and about 23% by dry fibrous structure weight of meltblown filaments. The line speed is adjusted to accumulate the fiber/filament blend to reach the desired basis weight. The batt is then gathered on a storage roll.

First Scrim Layer

Polymer resin blend: 21%: 27.5%: 47.5%: 4% blend, respectively, of PH835 polypropylene (LyondellBasell, London, UK): Metocene MF650W polypropylene (LyondellBasell, London, UK): Metocene MF650X (LyondellBasell, London, UK): White 412951 whitening agent/opacifier (Ampacet Corporation, Tarrytown, N.Y.).

The resin blend is heated to approximately 400° F.-405° F. in a melt extruder.

The melt extruder is used to feed the heated resin blend to a 15.5 inch wide Biax 12 row spinneret with 192 holes per cross-direction inch (Biax Fiberfilm Corporation, Greenville, Wis.) having 8 holes of the 192 holes per cross-direction inch with a 0.018 inch inside diameter melt outlet hole while the remaining nozzles are plugged.

The resin blend throughput in the spinneret is 0.18 grams per (open) hole per minute (ghm), i.e., 22.32 grams resin/minute through the spinneret.

Compressed attenuating air is supplied to the spinneret at a rate of 426 SCFM, heated such that it is at a temperature of 395° F. at the spinneret.

The attenuated filaments are water mist quenched using 2 misting nozzles, one on each broad side of the filament stream, each supplied with air at 35 psig and sufficient water supply for a flow rate of 2.5 gallons/hour.

Following mist quenching, the filaments are directed to a first foraminous belt supplied with vacuum, operating horizontally and carrying the previously-formed coformed core layer (unwound from its storage roll) and controlled to move at a machine direction speed of approximately 86 feet/minute; the filaments are accumulated over the core layer on a first side thereof to a basis weight of approximately 2 gsm.

Second Scrim Layer

A second scrim layer is formed by producing meltblown filaments in the same manner as for the first scrim layer as described above.

The previously-made core layer and overlying first scrim layer are released from the first foraminous belt, turned 90 degrees on a roller, and passed to a second foraminous belt operating vertically (also supplied with vacuum and moving at 92 feet/minute), to carry the core layer and first scrim layer, with the first scrim layer in facing contact with the second foraminous belt.

The filaments are directed toward the second foraminous belt and the core layer, to directly form a second scrim layer overlying the core layer, on a second side of the core layer.

Bonding

Following assembly of the three layers components of the fibrous web structure as described above, they are conveyed to the nip between a pair of calendar bonding rollers, adjusted to exert an amount of pressure on the batt in the nip suitable to form well-defined bonds without excessive material deformation beneath or about the bonding protrusions.

One bonding roller, which is heated to 250° F. at its surface, has pattern of bonding protrusions machined thereon in the pattern reflected in FIG. 10, and having a bonding area of 6.2 percent.

As they pass through the nip, the layers are consolidated in the z-direction and thermally bonded in the pattern to form a thermally bonded fibrous web structure.

Test Methods

Density Uniformity Index Method

The density uniformity index method measures the presence and dispersion of densified agglomerates within a fibrous web structure. A uniformity index of 1 indicates the highest degree of uniformity, with greater index values indicating less uniformity. It is based on analysis of projection x-ray images obtained on a FlashCT instrument (Hytec, Los Alamos, N. Mex.) or equivalent. The FlashCT is a cone beam microtomograph with a shielded walk-in cabinet. A dismountable Viscom microfocus x-ray tube is used as the source with an adjustable diameter focal spot. The transmitted x-rays pass through a collimator, a scintillator (Lanex regular) and onto a 30×40 cm Varian (Paxscan) amorphous silicon digital detector. The x-ray tube is an XT9225-DED with a maximum energy of 225 keV and a current range of 10 μA to 3000 μA. ZxAcquire software (ZaXa Software, Los Alamos, N. Mex. version 2.2.7.19365) or equivalent, is used to collect the images.

To obtain the samples to be measured, open a new package of wet wipes and remove the entire stack from the package. Discard the first 5 wipes from the top and bottom of the stack, and then remove 2 wipe samples from the top, middle and bottom of the stack, for a total of 6 wipe samples to be analyzed per package. A total of three packages should be measured, for a total of 18 samples. Lay the samples out flat and allow them to dry completely before analyzing.

Set up and calibrate the FlashCT instrument according to the manufacturer's specifications. Place the sample directly onto the detector and align the edges of the sample so that they are parallel to the detector's edges. Adhere the sample to the detector's surface, by taping down the sample's corners, without stretching the sample, so that it lays flat against the detector. The image should be collected at a resolution of 194 μm per pixel, or at a higher resolution and resized to that resolution prior to analysis. Images are acquired with the source at 45 kVp and 2000 μA with no additional low energy filter. The detector is 880 mm from the source and running at 5 frames per second, with 512 averages. The 2048×1536 pixel images are saved in 16-bit RAW format to preserve the full detector output signal for analysis. Continue to collect images until the source and detector has stabilized. After the system has stabilized, collect an image for analysis. Collect all subsequent images without any undue delay. If there is a delay, collect multiple images again until the instrument has restabilized prior to collecting additional images for analysis. Following the collection of an image with the sample on the detector, remove the sample and collect a corresponding blank image without a sample on the detector according to the same protocol.

To analyze the sample images, first open the saved 16-bit RAW image of the sample on the x-ray detector in ImageJ software (v. 1.47, National Institute of Health, USA). Crop out a 700 pixel by 700 pixel (135.8 mm by 135.8 mm) region of interest (ROI) from the center of the sample in the image. First, the sample image must be flattened and smoothed. Duplicate the image and apply a 50 pixel sigma radius Gaussian blur filter to the duplicate image. Using the image calculator, subtract the filtered duplicate image from the original image and produce a new flattened image with a 32-bit floating point result. Smooth the new flattened image with a 1 pixel median filter. Second, obtain a histogram of the flattened and smoothed image with 512 bins ranging from the minimum to the maximum values. Record the standard deviation of the image from the histogram output. Determine the graylevel value nearest to the $10^{th}$ percentile from a cumulative histogram. Third, threshold the image at the $10^{th}$ percentile graylevel value to generate a binary image. In the threshold image the more dense particles will appear as black and the surrounding structure as white. Select the analyze particles function, and set the minimum particle area exclusion limit to 2 pixels. Analyze the particles and record the particle count. Divide the particle count by the recorded standard deviation value to obtain the uniformity index value. Select and crop out a 700 pixel by 700 pixel (135.8 mm by 135.8 mm) ROI from the corresponding blank image at the same location at the ROI selected for the image with the sample, repeat this analysis and calculate the uniformity index value for the corresponding blank image. Calculate the ratio of the uniformity index value for the blank image to the uniformity index value of the corresponding sample and record this value as the density uniformity index value. Repeat this procedure on the remaining replicate samples (N=18), average the results and report the average density uniformity index value to the nearest 0.01.

Wet Versus Dry Uniformity Index Method

The wet versus dry wipe uniformity index is a measure of the visual discernibility of densified agglomerates within a wet fibrous web structure. A wet versus dry uniformity index less than 1.00 indicates an increase in visual uniformity as the structure dries, whereas a wet versus dry uniformity index value greater than 1.00 indicates a decrease in visual uniformity as the sample dries. It is based on analysis of the Lightness value of the CIE L*a*b* color system (CIELAB). A flatbed scanner capable of scanning a minimum of 24 bit color at 1200 dpi and has manual control of color management (a suitable scanner is an Epson Perfection V750 Pro from Epson America Inc., Long Beach Calif.) is used to acquire images. The scanner is calibrated against a color transparency target compliant to ANSI method IT8.7/1-1993 using color management software (a suitable package is MonacoEZColor available from X-Rite Grand Rapids, Mich.) to construct a scanner profile. The resulting calibrated scanner profile is applied to scanned images within an imaging program (a suitable program is Photoshop S4 available from Adobe Systems Inc., San Jose, Calif.) then converted to CIE L*a*b* and analyzed within ImageJ software (v. 1.47, National Institute of Health, USA).

To generate the scanner calibration profile, turn on the scanner for 30 minutes prior to calibration. Place the IT8 transmission target face down onto the scanner glass and close the scanner lid. Open the MonacoEZColor software and select acquire image using the Twain software included with the scanner. Within the Twain software deselect the unsharp mask setting and any automatic color correction or color management options that may be included in the software. If the automatic color management cannot be disabled, the scanner is not appropriate for this application. Acquire a preview scan at 200 dpi and 24 bit color in transparency mode (e.g. in the Epson software: Film with Film Area Guide—Positive Film setting). Insure that the scanned image is straight and first outer surface facing side-up. Crop the image to the edge of the target, excluding all white space around the target, and acquire the final image. The MonacoEZColor software uses this image to compare with included reference files to create and export a calibrated color profile compatible with Photoshop.

To obtain the samples to be measured, open a new package of wet wipes and remove the entire stack from the package. Discard the first 5 wipes from the top and bottom of the stack, and then remove 2 wipe samples from the top, middle and bottom of the stack, for a total of 6 wipe samples to be analyzed per package. A total of three packages should be measured, for a total of 18 samples. Without undue delay following the opening of the package, open the scanner lid and carefully place a wet sample flat on the center of the scanner glass. When placing the sample on the glass do not apply any additional pressure to avoid expressing any of the fluid out of the wipe. Place a frame with a 6 inch square opening on the sample and close the lid. Acquire and import a 5 inch by 5 inch scan of the sample from the interior of the frame into Photoshop at 300 dpi and 24 bit color in transparency mode. First assign the calibrated scanner profile to the image to perform the color correction, and then convert the image to an sRGB IEC61966-2.1 profile, ensuring that the "Intent" setting is set to Absolute calorimetric, and save it as a TIFF image. Lay the sample out flat and allow it to completely dry, and then repeat this procedure to obtain a corresponding image of the dry sample for comparison.

To analyze the sample images, first open the saved TIFF image of a wet sample in ImageJ software (v. 1.47, National Institute of Health, USA). Program ImageJ to convert the sRGB color space image into the CIE 1976 L*a*b*. This is two-step process, with the first step being the conversion of the sRGB to XYZ according to the mathematical conversion defined in IEC 61966-2-1:1999 using D65 as the reference white. The second step is the conversion from XYZ color space to CIE 1976 L*a*b* as defined in CIE 15:2004 section 8.2.1.1. Separate the L*a*b* stack into individual images, discard the a* and b* images and analyze only the L* image. First, the sample image must be flattened and smoothed. Duplicate the image and apply a 100 pixel sigma radius Gaussian blur filter to the duplicate image. Using the image calculator, subtract the filtered duplicate image from the original image and produce a new flattened image with a 32-bit floating point result to allow for negative values. Smooth the new flattened image with a 2 pixel median filter. Second, obtain a histogram of the flattened and smoothed L* image with 512 bins ranging from the minimum to the maximum L* values. Record the standard deviation of the image from the histogram output. List out the values from the histogram and determine the L* value nearest to the $10^{th}$ percentile from a cumulative L* histogram. Third, threshold the image at the $10^{th}$ percentile L* value to generate a binary image. In the threshold image the more opaque particles will appear as black and the surrounding structure as white. Set the scale of the image to 1500 pixels equal to 127 mm. Select the analyze particles function, and set the minimum particle area exclusion limit to 0.05 $mm^2$. Analyze the particles and record the particle count. Divide the particle count by the recorded standard deviation value to obtain the wet uniformity index value. Repeat this analysis on the corresponding dry sample image to obtain the dry uniformity index value. Calculate the wet versus dry uniformity index value by dividing the wet sample uniformity index value by the dry sample uniformity index value and record this value as the wet versus dry uniformity index value. Repeat this procedure on the remaining replicate samples (N=18), average the results and report the average wet versus dry uniformity index value to the nearest 0.01.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Background and Detailed Description are incorporated herein by reference to the extent not inconsistent with the specific disclosure herein; but the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wet wipe comprising a fibrous web structure wetted with an aqueous liquid composition, the fibrous web structure comprising:
   from 10 percent by weight to 40 percent by weight melt spun polymer filaments; and
   from 60 percent by weight to 90 percent by weight cellulose pulp fibers;
   wherein the fibrous web structure has one or both of:
   a Density Uniformity Index of from 3.00 to 6.00; and
   a Wet Versus Dry Uniformity Index of from 1.50 to 4.50;
   wherein a portion of the cellulose pulp fibers comprises visually discernable consolidated masses of the cellulose pulp fibers;
   wherein the wet wipe comprises a first outer scrim layer and a second outer scrim layer both comprising a first portion of the melt spun polymer filaments, and wherein the wet wipe comprises an inner core layer comprising the cellulose pulp fibers;
   wherein the first outer scrim layer has a basis weight from about 0.1 gsm to about 2.0 gsm; and
   wherein the second outer scrim layer has a basis weight from about 0.6 gsm to about 2.6 gsm.

2. The wet wipe of claim 1 wherein the fibrous web structure bears an impressed pattern of thermal bonds at which polymer filaments of each of the first and second outer scrim layers are deformed and fused.

3. The wet wipe of claim 1 wherein the inner core layer comprises a second portion of the melt spun polymer filaments.

4. The wet wipe of claim 3 wherein the second portion of melt spun polymer filaments comprises meltblown filaments.

5. The wet wipe of claim 1 wherein the first portion of melt spun polymer filaments comprises meltblown filaments.

6. The wet wipe of claim 5 wherein the meltblown filaments are mist-quenched.

7. The wet wipe of claim 1 wherein the cellulose pulp fibers comprise a blend of: fibers selected from the group consisting of short fibers, hardwood fibers, aspen fibers, birch fibers, *Eucalyptus* fibers, and combinations thereof; and fibers selected from the group consisting of long fibers, medium length fibers, softwood pulp fibers, SSK pulp fibers and combinations thereof.

8. The wet wipe of claim 1 wherein the cellulose pulp fibers comprise a blend of hardwood and softwood pulp fibers in a ratio of 60:40 to 90:10 by weight of softwood pulp fibers to weight of hardwood pulp fibers present in the fibrous web structure.

9. A wet wipe comprising a fibrous web structure wetted with an aqueous liquid composition, the fibrous web structure comprising:
   from 10 percent by weight to 40 percent by weight melt spun polymer filaments; and
   from 60 percent by weight to 90 percent by weight cellulose pulp fibers;
   wherein a portion of the cellulose pulp fibers comprises visually discernable consolidated masses of the cellulose pulp fibers;
   wherein the wet wipe comprises a first outer scrim layer and a second outer scrim layer both comprising a first portion of the melt spun polymer filaments, and wherein the wet wipe comprises an inner core layer comprising the cellulose pulp fibers; and
   wherein the second outer scrim layer has a basis weight from about 0.1 gsm to about 1.8 gsm.

10. The wet wipe of claim 9 wherein the consolidated masses comprise fibers selected from the group consisting of short pulp fibers, hardwood pulp fibers, aspen pulp fibers, birch pulp fibers, *Eucalyptus* pulp fibers and combinations thereof.

11. The wet wipe of claim 9 wherein the consolidated masses are visually discernible when the fibrous web structure has a water content of less than about 10% of the dry weight of the structure, and are of comparatively reduced visual discernibility when the fibrous web structure has a water content of 200% or more of the dry weight of the structure.

12. The wet wipe of claim 9 wherein the fibrous web structure bears an impressed pattern of thermal bonds at which polymer filaments of each of the first and second outer scrim layers are deformed and fused.

13. The wet wipe of claim 9 wherein the inner core layer comprises a second portion of the melt spun polymer filaments.

14. The wet wipe of claim 9 wherein the first portion of melt spun polymer filaments comprises meltblown filaments.

15. The wet wipe of claim 14 wherein the meltblown filaments have been mist-quenched following spinning.

16. The wet wipe of claim 9 wherein the cellulose pulp fibers comprise a blend of: fibers selected from the group consisting of short fibers, hardwood fibers, aspen fibers, birch fibers, *Eucalyptus* fibers, and combinations thereof and fibers selected from the group consisting of long fibers, medium length fibers, softwood pulp fibers, SSK pulp fibers and combinations thereof.

17. The wet wipe of claim 2 wherein the thermal bonds occupy from 2 percent to 12 percent of the surface area of the fibrous web structure on one side thereof.

18. The wet wipe of claim 1 wherein from about 1.0 percent by weight of the fibrous web structure to about 13 percent by weight of the fibrous web structure of the melt spun polymer filaments are allocated to the scrim layers.

19. The wet wipe of claim 9 wherein from about 1.0 percent by weight of the fibrous web structure to about 13 percent by weight of the fibrous web structure of the melt spun polymer filaments are allocated to the scrim layers.

20. A wet wipe comprising a fibrous web structure wetted with an aqueous liquid composition, the fibrous web structure comprising:
   from 10 percent by weight to 40 percent by weight melt spun polymer filaments; and
   from 60 percent by weight to 90 percent by weight cellulose pulp fibers;
   wherein a portion of the cellulose pulp fibers comprises visually discernable consolidated masses of the cellulose pulp fibers;
   wherein the wet wipe comprises a first outer scrim layer and a second outer scrim layer both comprising a first portion of the melt spun polymer filaments, and wherein the wet wipe comprises an inner core layer comprising the cellulose pulp fibers;
   wherein the second outer scrim layer has a basis weight from about 0.1 gsm to about 1.4 gsm; and
   wherein from about 1.0 percent by weight of the fibrous web structure to about 13 percent by weight of the fibrous web structure of the melt spun polymer filaments are allocated to the scrim layers.

21. The wet wipe of claim 1, wherein the visually discernable consolidated masses are spaced apart from each other.

* * * * *